United States Patent
Morado et al.

(10) Patent No.: US 12,338,210 B2
(45) Date of Patent: Jun. 24, 2025

(54) DEGRADABLE POLYMERS AND MONOMERS THEREFOR

(71) Applicant: The Board of Trustees of the University of Illinois, Urbana, IL (US)

(72) Inventors: Ephraim Gabriel Morado, Urbana, IL (US); Hsuan-Chin Wang, Lake in the Hills, IL (US); Steven Charles Zimmerman, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 504 days.

(21) Appl. No.: 17/217,512

(22) Filed: Mar. 30, 2021

(65) Prior Publication Data

US 2021/0317058 A1    Oct. 14, 2021

Related U.S. Application Data

(60) Provisional application No. 63/004,533, filed on Apr. 3, 2020.

(51) Int. Cl.
  *C07C 43/13*   (2006.01)
  *B01J 13/16*   (2006.01)
  (Continued)

(52) U.S. Cl.
  CPC ............. *C07C 43/135* (2013.01); *B01J 13/18* (2013.01); *C08F 20/06* (2013.01); *C08F 20/28* (2013.01);
  (Continued)

(58) Field of Classification Search
  None
  See application file for complete search history.

(56) References Cited

U.S. PATENT DOCUMENTS

| | | | | |
|---|---|---|---|---|
| 2,447,975 A | * | 8/1948 | Croxall | C08F 20/00 502/203 |
| 3,714,202 A | * | 1/1973 | Nakaguchi | C07D 317/14 549/453 |

(Continued)

OTHER PUBLICATIONS

Pivnick et al., "Methods for testing the germicidal value of chemical compounds for disinfecting soluble oil emulsions," Applied Microbiology, vol. 1, pp. 204-207 (1953) (Year: 1953).*

(Continued)

*Primary Examiner* — Ha S Nguyen
(74) *Attorney, Agent, or Firm* — Dilworth IP, LLC

(57) ABSTRACT

Hydroxyacetal or hydroxyketal monomers, processes for their preparation, their use to produce degradable polymers, hydroxy-functional intermediates resulting from degradation, and repurposed polymers made from the hydroxy-functional intermediates are described. The invention avoids the energy-intensive conditions normally used to degrade polyurethanes and generates new hydroxy-functional intermediates that can be repurposed or upcycled. Polyurethanes and melamines, materials once destined for a landfill, can have a second life. Incorporation of a photoacid generator into microcapsule core materials and fabrication of the shell from the hydroxy-functional acetal or ketal monomers promotes facile, inside-out, solid-state degradation of the microcapsule shell triggered by UV light and acid generation in a hydrophobic environment. This enables controlled release of flavors, fragrances, biocides, agricultural actives, or other oil-based beneficial agents from within the microcapsules.

15 Claims, 4 Drawing Sheets

(51) Int. Cl.

| | |
|---|---|
| *B01J 13/18* | (2006.01) |
| *C07C 41/26* | (2006.01) |
| *C07C 43/303* | (2006.01) |
| *C07C 271/20* | (2006.01) |
| *C08F 20/06* | (2006.01) |
| *C08F 20/28* | (2006.01) |
| *C08G 18/10* | (2006.01) |
| *C08G 18/32* | (2006.01) |
| *C08G 18/48* | (2006.01) |
| *C08G 18/76* | (2006.01) |
| *C08G 18/82* | (2006.01) |
| *C08G 71/04* | (2006.01) |
| *C08G 73/02* | (2006.01) |
| *C08J 11/16* | (2006.01) |
| *C08J 11/26* | (2006.01) |
| *C09D 7/41* | (2018.01) |
| *C09D 175/08* | (2006.01) |

(52) U.S. Cl.
CPC ......... *C08G 18/3206* (2013.01); *C08G 71/04* (2013.01); *C08G 73/0273* (2013.01); *C08J 11/26* (2013.01); *C07C 41/26* (2013.01); *C08G 2150/00* (2013.01); *C08G 2170/00* (2013.01); *C09D 7/41* (2018.01); *C09D 175/08* (2013.01)

(56) References Cited

U.S. PATENT DOCUMENTS

| | | |
|---|---|---|
| 4,808,689 A | 2/1989 | Katz |
| 6,825,377 B1 | 11/2004 | Beller et al. |
| 8,546,518 B2 | 10/2013 | Selifonov et al. |

OTHER PUBLICATIONS

Musavirov et al., "Preparation of di- and polyols by transacetalization of 1,3-dioxacyclanes," Zhurnal Prikladnoi Khimii, vol. 51(1), pp. 2295-2300 (1978) (Year: 1978).*
Bryan, J.D., "Linear acetal of ethylene glycol," Journal of Chemical Society, (1953) (Year: 1953).*
Nair et al., "Kinetics in biphasic catalysis using ethylene glycol as a co-solvent in the hydroformylation of 1-hexenel," Studies in Surface Science and Catalysis, vol. 113, pp. 529-539, (1998) (Year: 1998).*
Balashov, et al., "Exchange reaction of linear acetals with ethylene glycol by 13C NMR spectroscopy" Russian Journal of General Chemistry, vol. 69(9), pp. 1421-1426 (1999) (Year: 1999).*
Balashov, et al., "Features of acetal interchange of 1,1-dialkoxyalkanes with 1,2-propylene glycol in neutral solutions" Russian Journal of General Chemistry, vol. 71(5), pp. 752-755, (2001) (Year: 2001).*
Shostakovskii et al., "Reaction of vinyl and polyfunctional compounds. I. Reaction of vinyl alkyl ethers with glycerol," Bulletin of the Academy of Sciences of the USSR Division of Chemical, pp. 137-141 (1954) (Year: 1954).*
Shostakovskii et al., "Reactions of vinyl and polyfunctional compounds. III. Reaction of trivinyl glyceryl ether with ethylene glycol and 1,4-butylene glycol," Bulletin of the Academy of Sciences of the USSR Division of Chemical, pp. 583-587 (1954) (Year: 1954).*
Cunningham et al., "The Preparation of 1-O-Alk-1'-enyl Ethers of Glycerol," Journal of Chemical Society, p. 2968-2975, (1965) (Year: 1965).*
Wuts, "Green's Protective Groups in Organic Synthesis, 5th edition," p. 1-1332, (2014). (Year: 2014).*
Hashimoto et al., Synthesis of a new degradable polyurethane elastomer containing polyacetal soft segments, J. Polym. Sci. A 42 (2004) 2766.
Iinuma et al., Vinyl ether-based polyacetal polyols with various main-chain structures and polyurethane elastomers prepared therefrom: Synthesis, structure, and functional properties, J. Appl. Polym. Sci. 133 (2016) 44088.
Morado et al., Stimuli Responsive Polyurethane for Reprocessing and End-of-Life Repurposing, Oct. 7, 2019, 7 pages.
Ingier et al., Renewable thermoplastic polyurethanes containing rigid spiroacetal moieties, European Polymer Journal 70, (2015) 232-239.
Yang et al., Thermally Degradable Polyesters with Tunable Degradation Temperatures via Postpolymerization Modification and Intramolecular Cyclization, American Chemical Society Publications, Macromolecules, (2016) 49, 8449-8458.
Olejniczak et al., Light-Triggered Intramolecular Cyclization in Poly(lactic-co-glycolic acid)-Based Polymers for Controlled Degradation, American Chemical Society Publications, Macromolecules, (2015) 48, 3166-3172.
Paramonov et al., Fully Acid-Degradable Biocompatible Polyacetal Microparticles for Drug Delivery, Bioconjugate Chem., (2008) 19, 911-919.
Dewit et al., A Cascade Biodegradable Polymer Based on Alternating Cyclization and Elimination Reactions, J. Am. Chem. Soc., (2009) 131, 18327-18334.
Lux et al., Intramolecular Cyclization Assistance for Fast Degradation of Ornithine-Based Poly(ester amide)s, Journal of Polymer Science, Part A: Polymer Chemistry, (2013) 51, 3783-3790.
Kreye et al., Sustainable routes to polyurethane precursors, Green Chem., RSC Publishing, (2013) 15, 1431-1455.
Skarja et al., Structure-Property Relationships of Degradable Polyurethane Elastomers Containing an Amino Acid-Based Chain Extender, John Wiley & Sons, Inc., Journal of Applied Polymer Science, (2000) vol. 75, 1522-1534.
Zhang et al., Chemical Synthesis of Functional Poly(4-hydroxybutyrate) with Controlled Degradation via Intramolecular Cyclization, American Chemical Society Publications, Macromolecules, (2013) 46, 9554-9562.

\* cited by examiner

DEGRADABLE POLYMERS AND MONOMERS THEREFOR

FIELD OF THE INVENTION

The invention relates to degradable polymers and hydroxyacetal or hydroxyketal monomers used to make them.

BACKGROUND OF THE INVENTION

Polyurethanes are widely used to manufacture elastomers, coatings, foams, adhesives, and sealants with unique attributes. Because of their high durability, disposal of polyurethanes poses unusual challenges for landfills, oceans, and the environment in general. Currently, incineration at temperatures at or above 200° C. remains the most efficient disposal method despite its high energy consumption and environmental impact. Approaches to sustainable polyurethane products, which include reprocessing, mechanical breakdown, or chemical degradation, have so far been impractical to implement.

Various stimuli-responsive polymers that incorporate moieties able to undergo intramolecular cyclization can offer a promising approach to degradable polymers (see, e.g., M. DeWit et al., *J. Am. Chem. Soc.* 131 (2009) 18327; C. de Gracia Lux et al., *J. Polym. Sci., A, Polym. Chem.* 51 (2013) 3783; and A. Lv et al., *Macromolecules* 49 (2016) 8449). Although the results are inspiring, most of the polymers investigated in these studies lack much resemblance to polyurethanes. Degradable polyurethanes that incorporate acetal functionalities are known (see *Bioconjugate Chem.* 19 (2008) 911); the synthesis of these polymers is better suited to a laboratory-scale process.

Identifying practical ways to degrade polyurethanes is a worthy objective. However, a truly sustainable approach to achieving a circular polyurethane economy requires appropriate management of the post-degradation material. Recycling polyurethanes to generate the original building blocks (e.g., organic polyisocyanates) poses extraordinary challenges, but the right kind of degradation offers an opportunity to create new polymer intermediates, such as polyols, that can be repurposed or even upcycled to fulfill industry needs.

Microcapsules, conveniently made by known methods such as emulsion polymerization, provide a way to protect core materials until their release to the environment is desirable for applications such as biocides, fire retardants, herbicides, and fragrances. Controlling the mode and timing of release of the active materials is often a central concern. Triggering capsule degradation by various chemical, biological, thermal, photolytic, redox, and magnetic means is known, with pH- and light-triggered degradation offering great flexibility. Fréchet et al., for example, have developed acetal- and ketal-functional materials that can respond to and leverage pH gradients in biological systems (see, e.g., K. Broaders et al., *Chem. Commun.* 47 (2011) 665 and S. Pastine et al., *J. Am. Chem. Soc.* 131 (2009) 13586). A pH-based trigger is normally most applicable to aqueous systems. For solid-state degradation, a light trigger is desirable.

The industry would benefit from microcapsules that can degrade using pH, light, or some combination of these triggers to release core materials in a controlled and predictable way. Ideally, the microcapsules would have enhanced functionality, even in hydrophobic environments, and would utilize sustainable chemistries and polymer systems that advance the quest for a closed-loop economy.

SUMMARY OF THE INVENTION

In one aspect, the invention relates to a hydroxyacetal or hydroxyketal monomer. The monomer has the formula:

in which C is an acetal or ketal carbon. Each of $R^1$ and $R^2$ is hydrogen or a $C_1$-$C_{10}$ alkyl group or a $C_6$-$C_{10}$ aryl, aralkyl, or alkaryl group. X and Z are the same or different $C_3$-$C_{20}$ hydroxyalkyl or polyhydroxyalkyl groups such that: (a) each of X and Z has at least one hydroxyl group; (b) one or both of X or Z has two or more hydroxyl groups; and (c) one or both of the hydroxyalkyl or polyhydroxyalkyl groups has a free or protected hydroxyl group located on a carbon that is γ- or δ- to the acetal or ketal carbon.

In another aspect, the invention relates to hydroxyacetal or hydroxyketal monomers having the formula:

in which C is an acetal or ketal carbon; each of $R^1$ and $R^2$ is hydrogen or a $C_1$-$C_{10}$ alkyl group or a $C_6$-$C_{10}$ aryl, aralkyl, or alkaryl group; and X and Z are the same or different groups of the formula —$CH_2$—(CH)Y-L-Q, where Y is —OH or —$CH_2OH$, L is a linking group, and Q is a moiety comprising one or more —OH or —$NH_2$ groups.

The invention includes processes for making a hydroxyacetal or hydroxyketal tetrol monomer. One process comprises first reacting at least two equivalents of an unsaturated alcohol with an aldehyde or a ketone in the presence of an acidic catalyst to produce an acetal- or ketal-functional diolefin. The diolefin is then reacted with a dihydroxylating agent to produce the hydroxyacetal or hydroxyketal tetrol monomer. In another process, the tetrol monomer is produced without using a dihydroxylating agent from a 1,3-diester of trimethylolmethane, trimethylolethane, or trimethylolpropane.

In another aspect, the invention relates to a polyurethane or melamine product comprising one or more recurring units of the hydroxyacetal or hydroxyketal monomers described above. Such a polyurethane or melamine product is readily degradable and capable of generating a new hydroxy-functional polymer intermediate that can be repurposed. Thus, in another aspect, the invention includes a mixture comprising a hydroxy-functional intermediate wherein the mixture is made by acid-catalyzed degradation of the polyurethane or melamine product.

In yet another aspect, the invention relates to an acid-degradable polymer and to a mixture comprising a hydroxy-functional carbamate intermediate produced from the acid-degradable polymer. The acid-degradable polymer, which comprises recurring carbamate, hydroxyalkyl, and acetal or ketal units, has one or more free or protected hydroxyl groups located on a carbon that is γ- or δ- to an acetal or ketal carbon. In some aspects, this polymer is made by reacting an aminoalcohol or a polyamine with an acetal or ketal bis [alkylenyl(alkylene carbonate)].

In other aspects, the invention relates to a polyurethane coating, adhesive, sealant, elastomer, or foam made from the hydroxy-functional intermediate-containing mixtures described in the preceding two paragraphs. In other aspects, the invention relates to a melamine product made by reacting the hydroxy-functional intermediate-containing mixtures with hexakis(methoxymethyl)melamine, and to a radiation-curable resin made by reacting the mixtures with a (meth)acrylic acid or (meth)acrylate ester.

Although degradable polyurethanes that incorporate acetal functionalities were known, a practical way to make polyurethanes degrade even at room temperature has remained elusive. The invention harnesses intramolecular cyclization to avoid the energy-intensive conditions normally used to degrade polyurethanes or melamines. And whereas conventional approaches usually aim to regenerate the same starting materials from the high polymers, the invention generates new polymer intermediates that have hydroxyl functionality and can be repurposed to give new polyurethanes, melamines, or other high polymers. Consequently, the inventive approach is uniquely sustainable: it minimizes polluting side products by repurposing most of the degraded polymeric mixture to produce a new polyurethane coating, adhesive, or other useful product. Because polyurethanes and melamines made from the inventive monomers can be degraded under mild conditions, materials once destined for a landfill can have a second life.

In other aspects, the invention relates to UV light-degradable microcapsules. The capsules comprise a core and a degradable shell surrounding the core. The core comprises an oil-based active material and a photoacid generator. The degradable shell comprises a crosslinked polyamide or crosslinked polyester made by reacting a hydroxyacetal or hydroxyketal monomer as described above with a di- or polycarboxylic acid, ester, or halide in an aqueous emulsion under conditions effective to produce the light-degradable microcapsules.

Incorporation of the hydroxy-functional acetal or ketal monomers into the microcapsules promotes facile, inside-out, solid-state, degradation of the microcapsule shell triggered by UV light and acid generation in a hydrophobic environment. This enables controlled release of flavors, fragrances, coating indicators, sunscreens, biocides, agricultural actives, fire retardants, or other oil-based beneficial agents from within the microcapsules.

DETAILED DESCRIPTION OF THE INVENTION

Hydroxyacetal or Hydroxyketal Monomer

Figure 1:
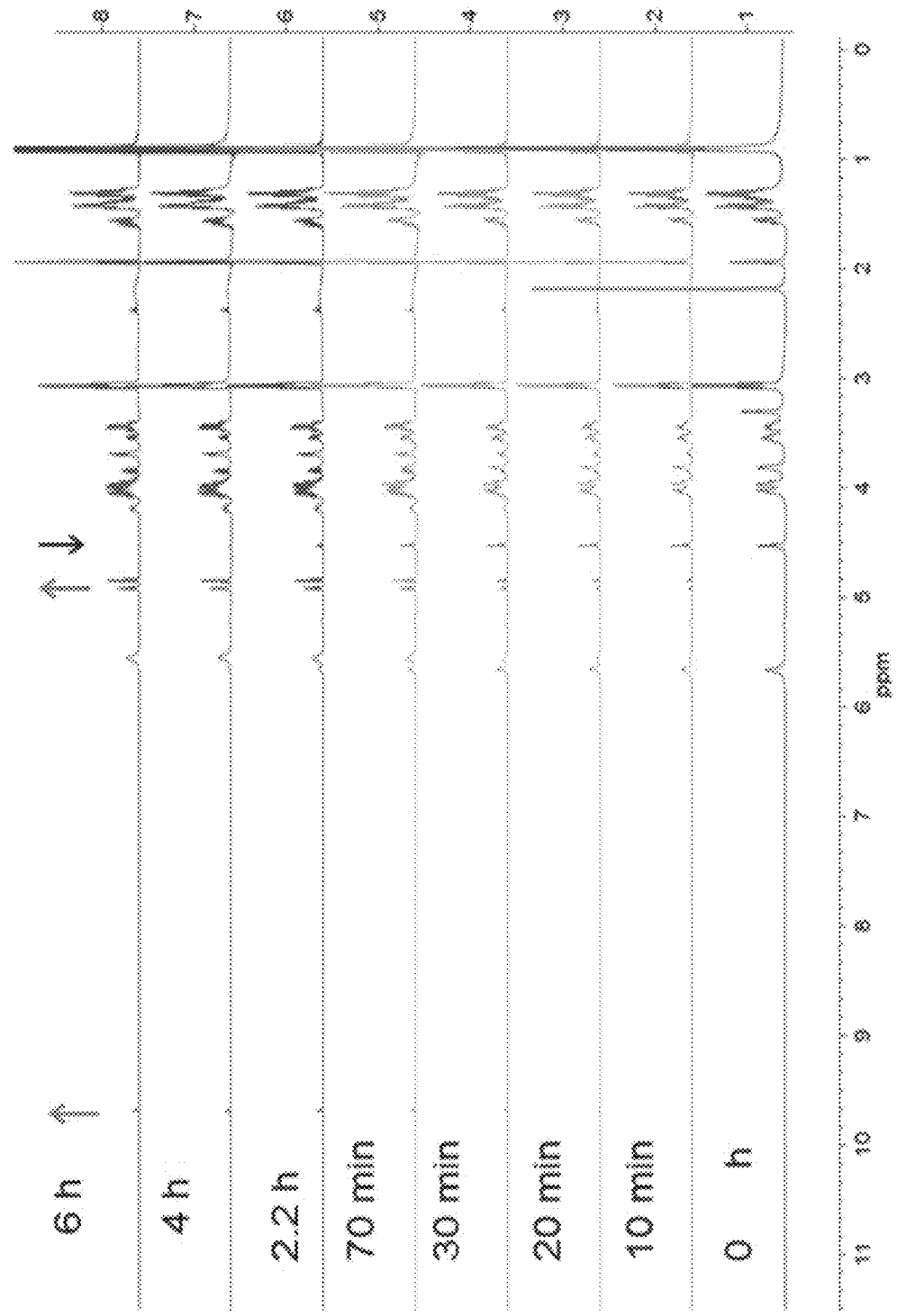
FIG. 1 shows stacked $^1$H NMR spectra showing degradation of bis(carbamate) 3 with p-toluenesulfonic acid in $CD_3CN$ (0.5 mol %) over 6 h.

In one aspect, the invention relates to a hydroxyacetal or hydroxyketal monomer. The monomer has the formula:

in which C is an acetal or ketal carbon. Each of $R^1$ and $R^2$ is hydrogen or a $C_1$-$C_{10}$ alkyl group or a $C_6$-$C_{10}$ aryl, aralkyl, or alkaryl group. In some aspects, the monomer is a hydroxyacetal in which $R^1$ is hydrogen and $R^2$ is a $C_1$-$C_{10}$ alkyl group or a $C_6$-$C_{10}$ aryl, aralkyl, or alkaryl group, especially a $C_1$-$C_{10}$ alkyl group.

X and Z are the same or different $C_3$-$C_{20}$ hydroxyalkyl or polyhydroxyalkyl groups. In some aspects, X and Z are identical. In some aspects, X and Z are the same $C_3$-$C_{12}$ hydroxyalkyl or polyhydroxyalkyl group, and $R^1$ is hydrogen. In some aspects, one or both of X and Z is a sugar residue.

X and Z satisfy three criteria: (a) each of X and Z has at least one hydroxyl group; (b) one or both of X or Z has two or more hydroxyl groups; and (c) one or both of the hydroxyalkyl or polyhydroxyalkyl groups has a free or protected hydroxyl group located on a carbon that is γ- or δ- to the acetal or ketal carbon.

When such a hydroxyacetal or hydroxyketal monomer is incorporated into a polyurethane or melamine product by reaction of two of its hydroxyl groups with the crosslinking agent (typically a polyisocyanate or hexakis(methoxymethyl)melamine), a free remaining hydroxyl group in the polyurethane or melamine product is available to promote acid-catalyzed degradation of the polymer (based on monomer requirements (a) and (b)). Monomer requirement (c), the need for "one or both of the hydroxy- or polyhydroxyalkyl groups" to have "a free or protected hydroxyl group located on a carbon that is γ- or δ- to the acetal or ketal carbon" ensures availability of a mechanism for a chain-breaking, acid-promoted intramolecular cyclization to generate a mixture that contains a new hydroxy-functional intermediate from the polyurethane or melamine product. The cyclization reaction is illustrated below for hydroxyl groups located either γ- or δ- to the acetal or ketal carbon:

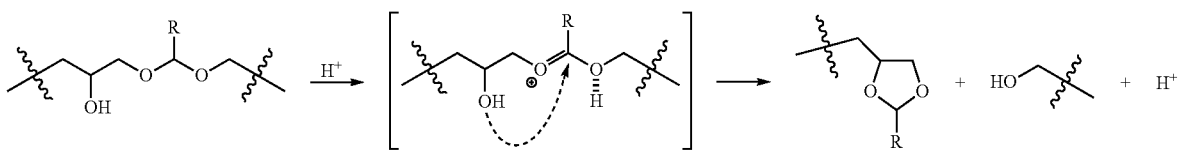

"Ready for intramolecular cyclization & cleavage"

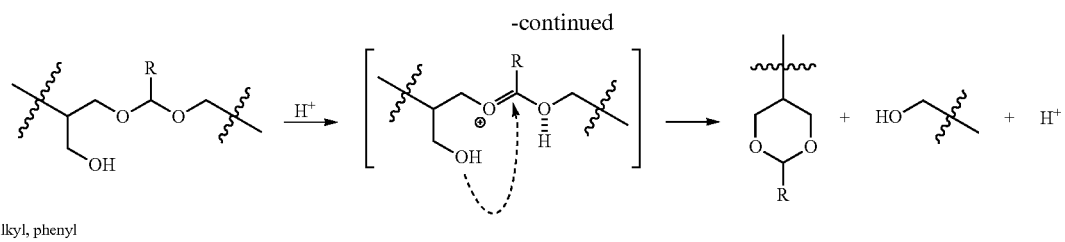

R = alkyl, phenyl

In some aspects, one or both of X or Z is a residue from glycerin, trimethylolmethane, trimethylolethane, trimethylolpropane, or diglycerol. In other aspects, one (but not both) of X or Z is a residue from ethylene glycol, propylene glycol, diethylene glycol, dipropylene glycol, triethylene glycol, tripropylene glycol, 2-methyl-1,3-propanediol, neopentyl glycol, 1,4-butanediol, or 1,6-hexanediol.

In some aspects, the monomer is a hydroxyacetal having a formula selected from:

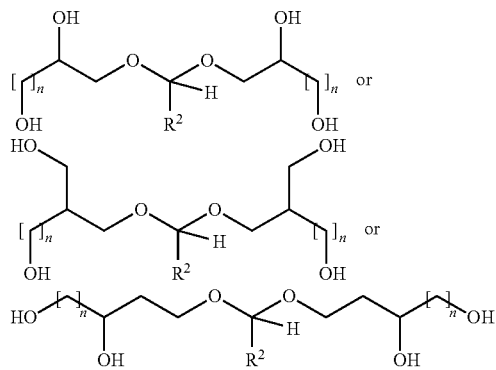

wherein n has a value from 1 to 10, or from 1 to 5, from 1 to 2, or 1.

In some aspects, the hydroxyacetal or hydroxyketal monomer has one or more protected hydroxyl groups. Suitable hydroxyl protecting groups are well known and are described, for example, in Peter G. M. Wuts, Greene's *Protective Groups in Organic Synthesis*, 5th Ed. (2014). Of interest for some applications are photocleavable protecting groups, such as o-nitrobenzyl or similar groups (see, e.g., J. Olejniczak et al., *Macromolecules* 48 (2015) 3166). Manufacture of the polyurethane or melamine product with such a monomer provides a product that, upon exposure to UV, generates a free hydroxyl group that can participate in the intramolecular cyclization/degradation process when the other criteria for the monomer are otherwise satisfied.

In some aspects, the hydroxyacetal or hydroxyketal monomer has the formula:

$$Z\text{—}O\text{—}(CR^1)R^2\text{—}O\text{—}X$$

in which C is an acetal or ketal carbon. Each of $R^1$ and $R^2$ is hydrogen or a $C_1$-$C_{10}$ alkyl group or a $C_6$-$C_{10}$ aryl, aralkyl, or alkaryl group. X and Z are the same or different groups of the formula —$CH_2$—(CH)Y-L-Q, where Y is —OH or —$CH_2$OH, L is a linking group, and Q is a moiety comprising one or more —OH or —$NH_2$ groups. Suitable L groups are divalent radicals, e.g., alkylene groups, that may incorporate one or more heteroatoms, heterocyclic groups, cycloaliphatic groups, aromatic rings, or may be used in combination with various functional groups, including amides, esters, ethers, carbamates, carbonates, or the like. In some aspects, L is a $C_1$-$C_8$ alkylene group. In other aspects, L includes a carbamate group. In the formula, Q is a moiety comprising one or more —OH or —$NH_2$ groups. The moiety commonly includes a $C_1$-$C_8$ alkylene group. In some aspects, Q is a residue of an alkanolamine and comprises one or two -OH groups.

In a specific aspect, the monomer has the formula:

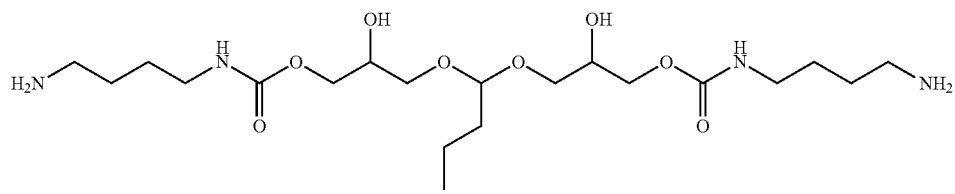 [SMILES: CCCC(OCC(O)COC(=O)NCCCCN)OCC(O)COC(=O)NCCCCN]

Process for Making Hydroxyacetal or Hydroxyketal Monomers

The invention includes processes for making certain hydroxyacetal or hydroxyketal monomers. One process comprises first reacting at least two equivalents of an unsaturated alcohol with an aldehyde or ketone in the presence of an acidic catalyst to produce an acetal- or ketal-functional diolefin. The diolefin is then reacted with a dihydroxylating agent to produce the hydroxyacetal or hydroxyketal tetrol monomer.

Suitable unsaturated alcohols have a carbon-carbon double bond and a hydroxyl group. In some aspects, the unsaturated alcohol is an allylic alcohol such as allyl alcohol or methallyl alcohol.

The dihydroxylating agent is a compound or mixture of compounds capable of converting a carbon-carbon double bond to a vicinal diol. In some aspects, the dihydroxylating agent comprises osmium tetroxide, potassium permanganate, or a mixture thereof. One suitable dihydroxylating agent uses an amine oxide such as N-methylmorpholine N-oxide as the principal oxidant in combination with a catalytic amount of osmium tetroxide (see, e.g., V. Van Rheenen et al., *Tetrahedron Lett.* 17 (1976) 1973).

In another inventive process, the hydroxyacetal or hydroxyketal monomer is prepared without the need for a dihydroxylating agent. In this process, a 1,3-diester from trimethylomethane, trimethylolethane, or trimethylolpropane, preferably a 1,3-diacetate, is reacted with an aldehyde or a ketone to produce an acetal- or ketal-functional tetraester, preferably a tetraacetate. The tetraester is then hydrolyzed under basic conditions (e.g., aqueous NaOH, KOH, or LiOH) to produce the hydroxyacetal- or hydroxyketal tetrol monomer. The 1,3-diesters are easy to prepare by well-known methods for converting hydroxyl groups to esters, e.g., the reaction with acetic anhydride to give acetate esters. Example 2A, below, illustrates this osmium-free approach to the tetrol.

Acid-Degradable Polyurethanes or Melamines

In another aspect, the invention relates to acid-degradable polyurethanes or melamines comprising one or more recurring units of a hydroxyacetal or hydroxyketal monomer as described above.

Acid degradability results from incorporation of the acetal or ketal moiety into the polyurethane or melamine high polymer. In general, mild, subtle, or intermittent acidic conditions (such as exposure to acid rain at pH 3.5 to 5.5) will be insufficient to substantially degrade the polyurethane or melamine absent a prolonged time period. Generally, it is more desirable to purposefully degrade the polyurethane or melamine product during a short, predictable timeframe, preferably at or about room temperature, under reasonably mild conditions. We found that the inventive monomers can be used to produce polyurethanes or melamines that can degrade at room temperature within several hours when combined with an organic solvent capable of swelling the polymer (e.g., dichloromethane) and a relatively strong acid. In some aspects, the acid will have a pka less than 3.0, less than 2.0, or ideally less than 1.0. Trichloroacetic acid (pKa=0.7) and methanesulfonic acid (pKa-1.9) work well for this purpose.

Aside from incorporation of the hydroxyacetal or hydroxyketal monomer, the polyurethanes otherwise resemble those commonly made from well-known and commercially available di- or polyisocyanates (e.g., TDI, MDI, polymeric MDI, aliphatic di- or polyisocyanates, or the like), polyols (polyether polyols, polyester polyols, polycarbonate polyols, or the like), and chain extenders (ethylene glycol, 1,4-butanediol, ethylenediamine, or the like). In preferred aspects, the polyurethanes are linear such that degradation effectively cleaves chains and reduces molecular weight. The polyurethanes can include one or more urea or other functionalities in addition to their urethane (carbamate) content.

Suitable melamines also resemble products from well-known starting materials aside from incorporation of the hydroxyacetal or hydroxyketal monomer. In some aspects, the melamine is a reaction product of one or more polyols and/or chain extenders as described above and hexakis (methoxymethyl)melamine.

The polyurethanes or melamines need not have a high proportion of the hydroxyacetal or hydroxyketal monomer to be degradable. However, the amount of monomer needed to achieve a desired degradation profile will depend on many factors within the skilled person's discretion, including, for example, the intended use of the polyurethane or melamine, the degree of crosslinking in the polyurethane or melamine, the reactants and proportions used to make the polyurethane or melamine, the reagents and conditions expected to be used for degrading the polymers, the desired degradation rate, and other factors. In general, the content of the hydroxyacetal or hydroxyketal monomer will typically range from 0.01 to 15 wt. %, or from 0.1 to 8 wt. %, or from 0.5 to 4 wt. %, based on the amount of polyurethane or melamine material.

Degraded Mixtures

The invention includes mixtures produced by acid-catalyzed degradation of the inventive polyurethanes or melamines described above. These relatively crude mixtures will comprise, among other components, a hydroxy-functional intermediate (or a cyclic acetal/cyclic ketal precursor). The mixtures may also contain aldehydes or ketones liberated from the acetals or ketals (respectively), the acid used to degrade the polyurethane or melamine product, one or more solvents, and any side products, such as aldol condensation products.

The structure of the hydroxyacetal or hydroxyketal monomer is designed to enable an intramolecular cyclization reaction that not only disconnects the high polymer chain of the polyurethane or melamine, but also generates new functionality in the form of a cyclic acetal having a five- or six membered ring. Decomposition of this cyclic acetal under aqueous acidic conditions generates free hydroxyl groups on both liberated chain ends, thereby producing a new "polyol" capable of being repurposed in a coating, elastomer, foam, adhesive, or other end use.

In Example 6, below, the initial acid-catalyzed intramolecular cyclization reaction using a model bis(carbamate) compound is illustrated. The goal was to be able to study the rate of chain disconnection in a simple system using $^1$H NMR spectroscopy.

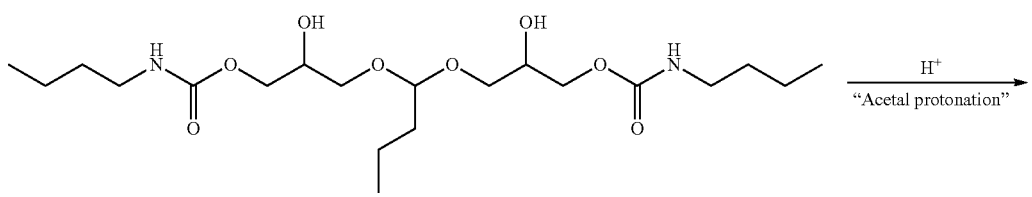

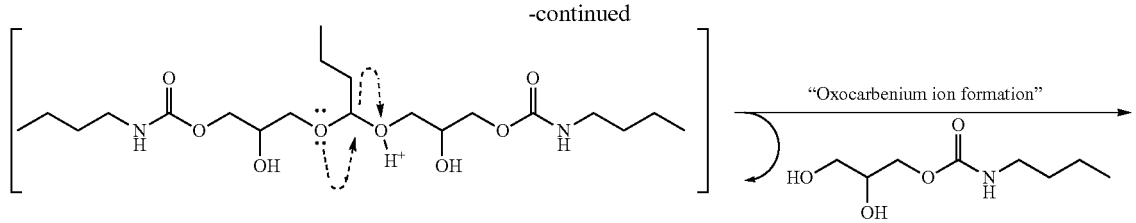

"Oxocarbenium ion formation"

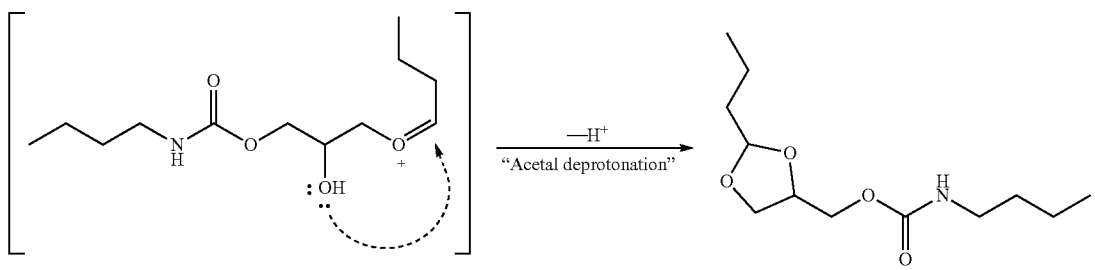

"intramolecular cyclization"

A free hydroxyl group located (in this case) on a carbon that is γ- to the acetal carbon participates in generating a new 5-membered cyclic acetal upon intramolecular cyclization. As shown in Example 6 and FIG. 1, the acetal proton of the bis(carbamate), initially a triplet at 4.33 ppm, disappears over 6 h, and a new signal at 4.90 ppm (doublet of doublets) corresponding to formation of a new acetal proton on the 2-propyl-1,3-dioxolane ring emerges. The model experiment demonstrates successful degradation using a model compound instead of a high polymer. However, an analogous reaction occurs when a high polymer is used instead of the model compound.

The steps needed and degree of purification desirable for the degraded mixture will depend on the source of the polyurethane or melamine, the conditions and reagents used to degrade it, the nature of the repurposed product, the desired end use, and other factors that will be known to the skilled person. Usually, the degraded mixture will be washed or otherwise treated to neutralize and/or remove the acidic catalyst (used to degrade the polyurethane or melamine) prior to its use in a repurposed product. In some aspects, a straightforward organic workup, such as the one described below in Example 10, will suffice. Thus, the degraded mixture can be diluted in an organic solvent, washed with a base, dried, and concentrated to give a neutralized crude mixture that contains the hydroxy-functional intermediate. In some aspects, the initial acid treatment generates a precursor to the hydroxy-functional intermediate in the form of a 5- or 6-membered ring acetal or ketal. As Example 10 shows, a second acid treatment can then be used to convert the precursor into its corresponding hydroxy-functional intermediate. The hydroxy-functional intermediates will have a vicinal diol at one chain end when the original free hydroxyl group is located γ- to the acetal or ketal carbon or a 1,3-diol at one chain end when the original free hydroxyl group is located δ- to the acetal or ketal carbon.

In some aspects, the invention relates to an acid-degradable polymer comprising recurring carbamate, hydroxyalkyl, and acetal or ketal units, wherein the polymer has one or more free or protected hydroxyl groups located on a carbon that is γ- or δ- to an acetal or ketal carbon. Suitable acid-degradable polymers of this type can be made by reacting an aminoalcohol or a polyamine with an acetal or ketal bis[alkylenyl(alkylene carbonate)].

For example:

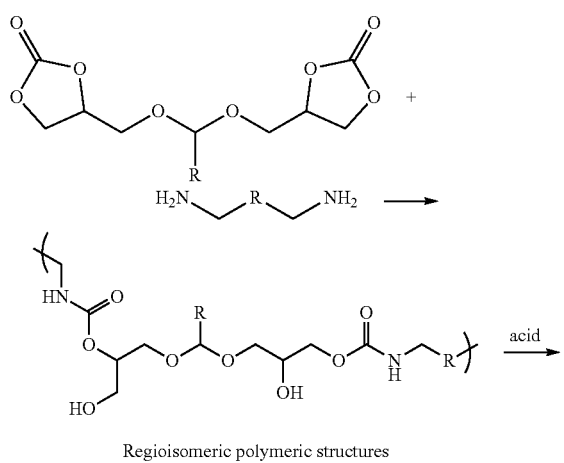

Regioisomeric polymeric structures

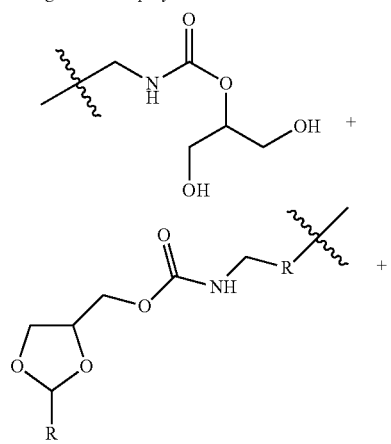

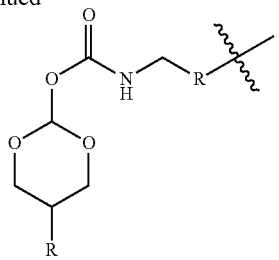

Another convenient way to make the acid-degradable carbamate polymer in two reaction steps:

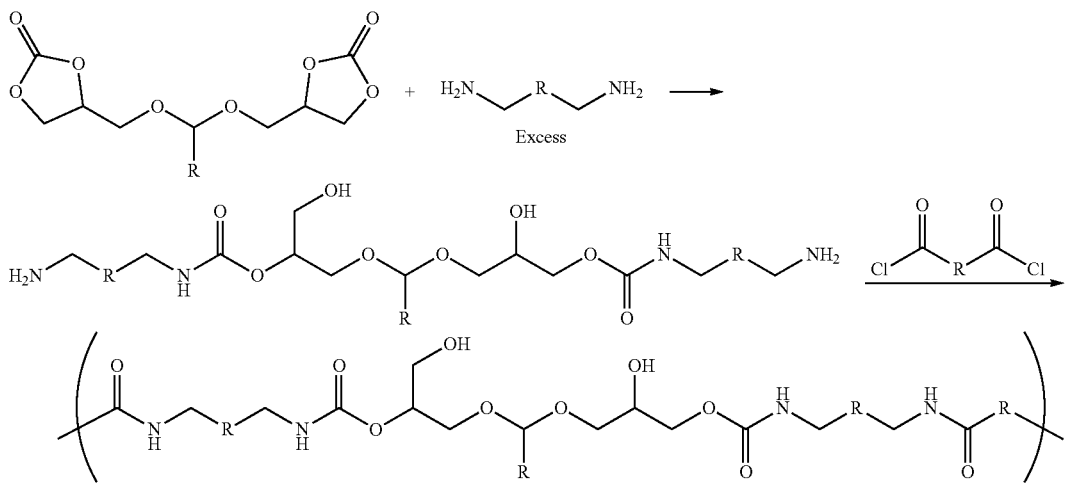

As was the case for the acid-degradable polymers discussed earlier, these polymers can be degraded under acidic conditions to produce cyclic acetal/ketal precursors to (in this case) hydroxy-functional carbamate intermediates. The hydroxy-functional carbamate intermediates can then be repurposed (as described below) to make new polyurethanes, melamines, acrylate resins, and other useful "second life" products. Non-degradable carbamate polymers of this type, i.e., ones that lack any acetal or ketal functionality and can be made by reacting polyamines with bis[alkenyl(alkylene carbonates)], have been described elsewhere (see, e.g., O. Kreye et al., *Green Chem.* 15 (2013) 1431 at p. 1443); these were originally conceived as a "phosgene-free" (non-isocyanate) route to urethanes.

Repurposed Products

Whereas simply degrading waste polyurethanes and other materials is a laudable goal, a more sustainable approach repurposes the degraded material for a second useful life. The inventive acid-degradable polymers are well-suited for this purpose. We found that the mixtures comprising a hydroxy-functional intermediate (or hydroxy-functional carbamate intermediate), following any appropriate clean-up, are useful for making polymers for other end uses. These uses include the production of new polyurethanes, new melamines, radiation-curable acrylate polymers, polyesters, or other high polymers that utilize hydroxy-functional intermediates.

For instance, we found that an elastomer fabricated from a commercial TDI-based prepolymer and an inventive hydroxyacetal or hydroxyketal monomer degrades at room temperature in dichloromethane in the presence of trichloroacetic acid. Following a simple workup, the concentrated mixture comprising a hydroxy-functional intermediate is suitable for use in making a polymeric MDI-based polyurethane adhesive with good lap-shear strength (see Example 11) or a spiropyran dye-infused photochromic coating (Example 12). Success in these rapid screening experiments suggests that the inventive degraded mixtures will have potential value for a wide range of applications for which hydroxy-functional polymer intermediates are needed.

Examples of such applications include polyols for making polyurethanes, polyisocyanurates, polyurethane-polyureas, polyesters, melamines, radiation-curable resins, and other products. Suitable products include flexible foams, molded foams, rigid foams, coatings, one- or two-component adhesives, elastomers, sealants, and other traditional polyol applications.

Melamine products are conveniently made by reacting the mixture comprising the hydroxy-functional intermediate or the hydroxy-functional carbamate intermediate with hexakis(methoxymethyl)melamine according to well-known methods.

A radiation-curable resin can be made by esterifying the mixture comprising the hydroxy-functional intermediate or the hydroxy-functional carbamate intermediate with acrylic acid or methacrylic acid or by transesterifying the mixture with an acrylate or methacrylate ester, especially a $C_1$-$C_4$ alkyl acrylate or methacrylate.

Degradable Microcapsules

In some aspects, the invention includes UV light-degradable microcapsules comprising a core and a degradable shell surrounding the core. The core comprises an oil-based active material and a photoacid generator. The degradable shell comprises a crosslinked polyamide or crosslinked polyester that is made by reacting a hydroxyacetal or hydroxyketal monomer as described above with a di- or polycarboxylic acid, ester, or halide in an aqueous emulsion under conditions effective to produce the light-degradable microcapsules. When the monomer has terminal amino groups, reaction with the di- or polycarboxylic acid, ester, or halide, preferably a halide, generates a crosslinked polymer shell having polyamide functionality. When the monomer has only terminal hydroxyl groups, reaction with the di- or polycarboxylic acid, ester, or halide, again preferably a halide, generates a crosslinked polymer shell having polyester functionality. For many applications, microcapsules having polyamide functionality are preferred because they are relatively straightforward to synthesize and are robust.

Suitable methods for preparing the microcapsules by interfacial polymerization, for instance, by reacting diamines and trimesoyl chloride, have been described previously by Fréchet and coworkers (discussed, supra). Generally, an organic phase comprising the di- or polycarboxylic acid, ester, or halide, preferably a tricarboxylic acid halide such as trimesoyl chloride, is emulsified with aqueous polyvinyl alcohol solution. For making the inventive microcapsules, a photoacid generator (PAG) is included in the organic phase. An aqueous mixture containing the hydroxyacetal or hydroxyketal monomer, which has hydroxyl or both hydroxyl and amino groups, is then added slowly to the well-agitated emulsion. When the monomer has amino groups and an acid chloride reactant is used, the reaction usually proceeds rapidly at room temperature. When only hydroxyl groups are present in the monomer and/or a carboxylic acid or ester reactant is used, heating will usually be needed to make the microcapsules. Example 19, below, shows one suitable method for making degradable microcapsules.

The PAG is a compound that produces halide radicals (especially bromine or chlorine radicals) upon exposure to UV light at 365 nm. Compounds having trichloromethyl or tribromomethyl groups, particularly compounds having extended conjugation to stabilize radicals through resonance, are known PAGs. Examples include trihalomethyl-substituted aromatic compounds (e.g., 1,3,5-tris(trichloromethyl)benzene, 1,3-bis(trichloromethyl)benzene, or 1,3,5-trifluoro-2,4,6-tris(trichloromethyl)benzene), especially trihalomethyl-substituted triazines such as 2-(4-methoxystyryl)-4,6-bis(trichloromethyl)-1,3,5-triazine (used in Example 19), 2-methyl-4,6-bis(trichloromethyl)-1,3,5-triazine, and 4,6-bis(trichloromethyl)-1,3,5-triazine.

The microcapsules, once formed, are typically collected and rinsed successively with water and volatile organic solvents (e.g., acetone, diethyl ether) to remove surface impurities.

The inventive microcapsules uniquely include the PAG, which enables inside-out degradation of the microcapsule shell upon exposure to light and generation within the capsule of a mineral acid, typically HCl or HBr. Chlorine or bromine atoms, generated by homolytic cleavage of C—Cl or C—Br bonds in the PAG, abstract hydrogen atoms from the shell polymer or core materials to form the acid. The oil-based core material, which could be a flavor, a fragrance, a coating indicator, a sunscreen, a biocide, an agricultural active, a fire retardant, or another beneficial agent, is liberated from the core when the microcapsule shell degrades. The hydroxyacetal or hydroxyketal monomers facilitate shell degradation by providing neighboring hydroxyl groups that are in position to promote cyclic acetal formation by a mechanism consistent with "CATCH cleavage":

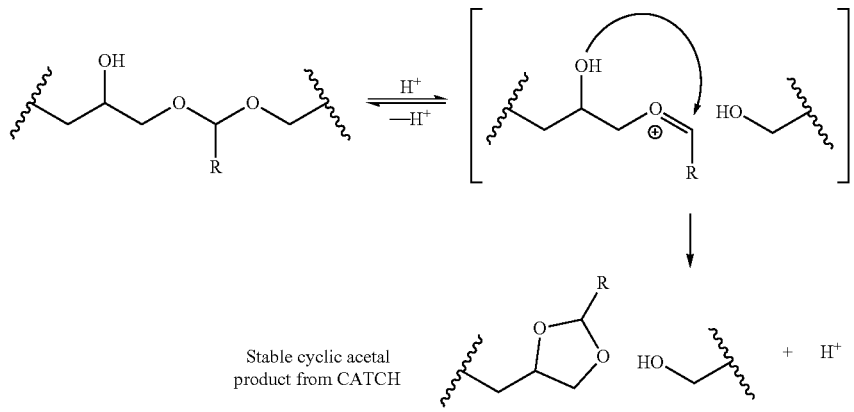

Stable cyclic acetal product from CATCH

The following examples merely illustrate the invention; the skilled person will recognize many variations that are within the spirit of the invention and scope of the claims.

Example 1

Preparation of Bis(allyl)acetal 1

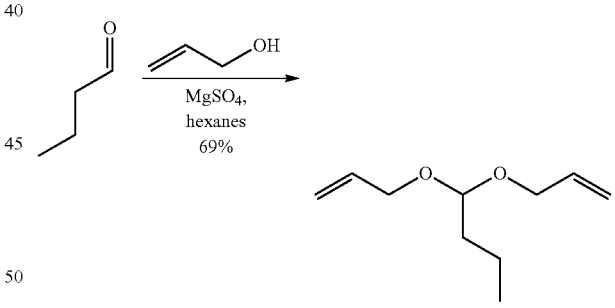

Allyl alcohol (85.4 g, 100 mL, 1.47 mol) and butyraldehyde (53.0 g, 66.3 mL, 0.736 mol) are combined with hexanes (500 mL) in a 1-L round-bottom flask. The mixture is magnetically stirred as $MgSO_4$ (50 g) and p-toluenesulfonic acid monohydrate (2.64 g, 13.9 mmol) are added. The mixture is heated with stirring at 50° C. under nitrogen for 12 h. Reaction progress is monitored using thin-layer chromatography using (1:2 v:v dichloromethane:hexanes) until complete. Triethylamine (1.4 g, 2.0 mL, 14 mmol) is added, and the mixture is stirred for 1 h. The product is filtered, and the organic layer is dried under reduced pressure to obtain a yellow oil. The crude product is vacuum distilled to yield a clear oil (86.0 g, 69%). $^1$H NMR (400 MHZ, CDCl$_3$): δ 5.92

(m, 2H), 5.29 (ddq, J=17, 3.3, 1.8 Hz, 2H), 5.16 (dtd, J=10.4, 3.5, 3.0, 1.5 Hz, 2H), 4.61 (td, J=5.5, 1.9 Hz, 1H), 4.06 (m, 4H), 1.63 (m, 2H), 1.40 (m, 2H), 0.93 (td, J=7.7, 2.8 Hz, 3H). $^{13}$C NMR (500 MHZ, CDCl$_3$): δ 135.0, 116.8, 102.2, 66.3, 35.6, 18.2, 14.1.

Example 2

Preparation Acetal-Functional Tetrol 2

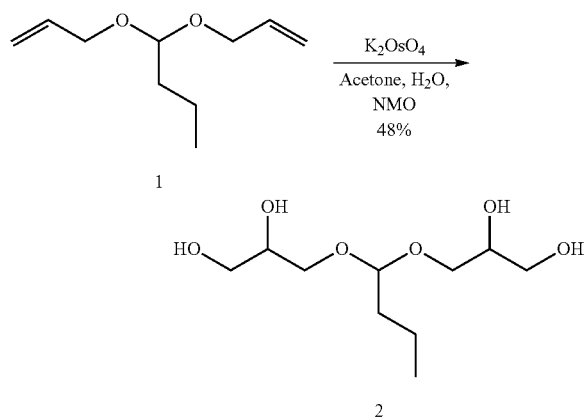

A 1-L round-bottom flask is charged with 1,1-bis(allyloxy) butane (86.0 g, 505 mmol), t-butanol (20 mL), acetone (100 mL), and N-methylmorpholine N-oxide ("NMO," 50 wt. % solution in water, 320 g). Potassium osmate(VI) dihydrate (520 mg, 2.04 mmol) is added, and the reaction mixture is stirred for 24 h. The reaction is quenched by adding Na$_2$SO$_3$ (50 g) solids. The black mixture becomes a light brown, clear solution. The reaction product is extracted with ethyl acetate (4×500 mL). The organic layer is washed with brine (4×100 mL), dried with sodium sulfate, filtered, and concentrated to obtain a yellow oil. Flash column chromatography (silica gel, ethyl acetate/hexanes from 10:80 to 100% EtOAc) affords the desired tetrol as a yellow oil (58.0 g, 48%). $^1$H NMR (400 MHZ, CDCl$_3$): δ 4.55 (tt, J=5.8, 2.8, Hz, 1H), 3.87 (d, J=70 Hz, 2H), 3.62 (m, 10H), 3.18 (s, 2H), 1.62 (ddq, J=11, 5.5, 2.8, Hz, 2H), 1.37 (dqd, J=9.7, 7.4, 5.5 Hz, 2H), 0.93 (t, J=7.4 Hz, 3H). $^{13}$C NMR (500 MHZ, CDCl$_3$): δ 104.0, 71.0, 67.4, 63.8, 35.3, 18.1, 14.0. M/z by HRMS (ESI+) calculated for C$_{10}$H$_{23}$O$_6$ [M+H]$^+$: 239.1; found: 239.1.

Example 2A

Preparation Acetal-Functional Tetrol 2a

An osmium-free route to a tetrol 2a from trimethylolethane using acetyl protecting groups is described below.

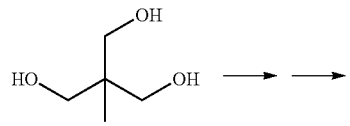

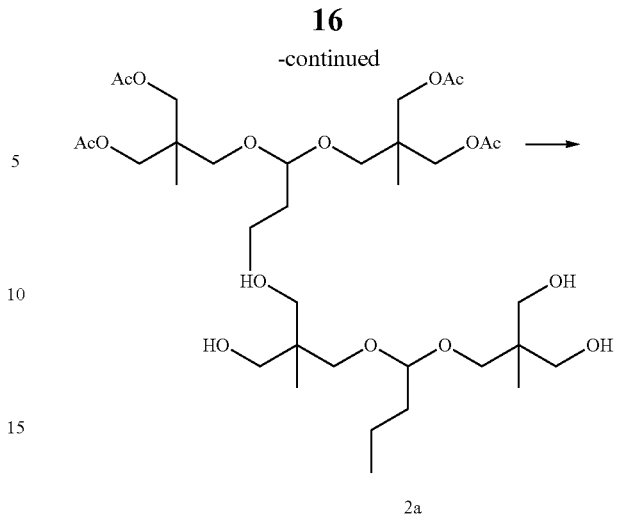

Triethylamine (40.5 mL, 291 mmol, 3.5 equiv.) is added to trimethylolethane (10.0 g, 83 mmol, 1 equiv.) in THF (250 mL), and the reaction mixture is allowed to stir for 20 min. Acetic anhydride (16.5 mL, 200 mmol, 2.4 equiv.) is added dropwise at 0° C., and the mixture is warmed to room temperature and stirred under nitrogen for 20 h. The solution is concentrated in vacuo. The residue is redissolved in ethyl acetate (200 mL) and washed with 1 M HCl (3×100 mL), followed by brine (2×100 mL). This solution is dried with Na$_2$SO$_4$ and concentrated. Flash column chromatography (silica gel, ethyl acetate:hexanes, 30:70) gives a clear, yellow oil (6.36 g, 37%), which gives spectra consistent with the desired trimethylolethane 1,3-diacetate product. $^1$H NMR (400 MHZ, CDCl$_3$) δ 4.01 (s, 4H), 3.41 (s, 2H), 2.39 (s, 1H), 2.08 (s, 6H), 0.95 (s, 3H).

The diacetate (6.00 g, 29.4 mmol, 3.0 equiv.) and butyraldehyde (0.9 mL, 9.8 mmol, 1 equiv.) are dissolved in hexanes (60 mL). Anhydrous magnesium sulfate (12 g, 100 mmol, 10 equiv.) is added to the solution, which is then cooled to 0° C. A solution of p-toluenesulfonic acid monohydrate in THF (0.1 M, 4.9 mL, 0.49 mmol, 0.050 equiv.) is added dropwise. The reaction mixture is warmed to room temperature and stirred under nitrogen for 27 h. The crude reaction mixture is quenched with triethylamine (8.0 mL), stirred for 20 min., and filtered. The filtrate is concentrated in vacuo, redissolved in MeOH (30 mL), and added to saturated aq. NaHCO$_3$ (30 mL). Deionized water (20 mL) is added, and the product is extracted with hexane (2×25 mL). The organic layers are washed with saturated aq. NaHCO$_3$, deionized water, and brine (25 mL each), then dried over Na$_2$SO$_4$ and concentrated in vacuo. Flash column chromatography (silica gel washed with 1% triethylamine in the mobile phase, EtOAc:hexanes, 30:70) provides the expected butyraldehyde acetal tetraacetate product (2.0 g, 44%). $^1$H NMR (500 MHZ, CDCl$_3$) δ 4.41 (t, J=5.8 Hz, 1H), 3.99 (s, 8H), 3.33 (dd, J=101.3, 9.3 Hz, 4H), 2.06 (s, 12H), 1.54 (m, 2H), 1.31 (sext, J=7.6 Hz, 2H), 0.98 (s, 6H), 0.90 (t, J=7.4 Hz, 3H).

A portion of the butyraldehyde acetal tetraacetate (0.50 g, 1.08 mmol, 1 equiv.) is dissolved in dioxane (3 mL). Deionized water (3 mL) and lithium hydroxide (0.83 g, 35 mmol, 32 equiv.) are added. The reaction mixture is stirred under nitrogen at 60° C. for 16 h. After cooling to room temperature, 1 M HCl is added dropwise until the reaction mixture reaches a pH of 7. The product is extracted with ethyl acetate (2×30 mL), and the combined organic layers are washed with deionized water and brine (30 mL each), dried with Na₂SO₄, and concentrated in vacuo. Flash column chromatography (silica gel washed with 1% triethylamine in mobile phase, MeOH:dichloromethane, 10:90) gives the desired acetal-functional tetrol monomer, 2a (0.18 g, 57%). $^1$H NMR (500 MHz, CDCl₃) δ 4.54 (t, 5.8 Hz, 1H), 3.80-3.33 (m, 12H), 1.65 (m, 2H), 1.39 (m, 2H), 0.95 (t, J=7.4 Hz, 3H), 0.83 (s, 6H).

Example 3

Preparation of Bis(carbamate) 3

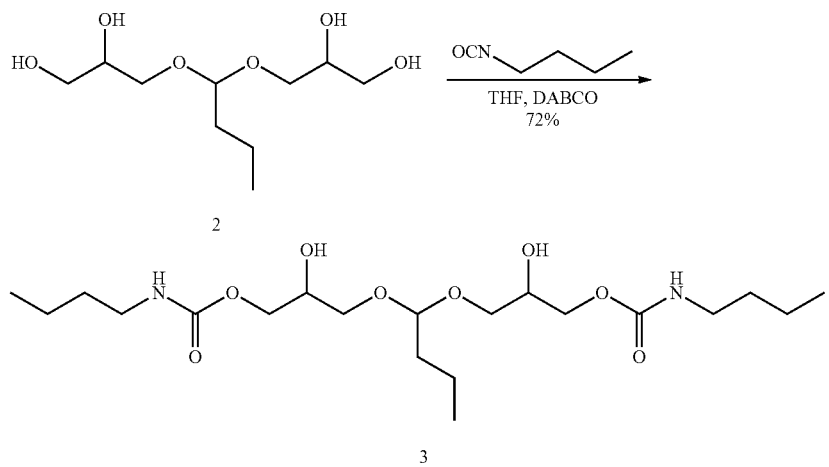

Acetal-functional tetrol 2 (477 mg, 2.0 mmol), 1,4-diazabicyclo[2.2.2]octane ("DABCO," 8.0 mg), and dichloromethane (1.0 mL) are combined in a small flask and stirred under nitrogen. N-Butylisocyanate (0.45 mL, 4.0 mmol) is added to the mixture by syringe, and the reaction continues at room temperature for 1 h. The mixture is concentrated, and the crude product is purified by flash column chromatography (silica gel, ethyl acetate:hexanes from 10:80 v:v to 100% EtOAc) to obtain a clear oil (86 mg, 72%). $^1$H NMR (DMSO-d₆): δ 5.23 (s br, 2H), 4.58-4.51 (m, 1H), 4.26-4.06 (m, 4H), 4.02-3.90 (m br, 2H), 3.66-3.48 (m, 4H), 1.46 (pentet, J=7.5, 4H), 1.32 (sextet, J=7.5, 6H), 0.90 (t, J=7.5, 9H). $^{13}$C NMR (CDCl₃): δ 157.2-157.0, 103.4-103.1, 69.7-39.3, 66.3-65.8, 60.5, 40.9, 35.1, 32.0, 20.0, 18.0, 14.3. M/z by HRMS (ESI+) calculated for C₂₀H₄₀N₂O₈Na [M+Na]⁺: 459.2; found: 459.2.

Comparative Example 4

Preparation of Ethylene Glycol Bis(Allyl Ether) 4

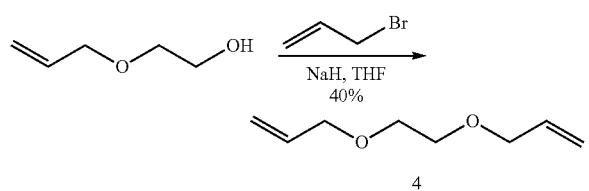

2-Allyloxyethanol (14.3 g, 15 mL, 0.14 mol) is dissolved in THF (20 mL) in a round-bottom flask. Sodium hydride (60% NaH in mineral oil, 4.4 g, 0.11 mol) is added portionwise, and the mixture is magnetically stirred for 1 h. Allyl bromide (97%, 19.4 mL, 0.22 mol) is added slowly by syringe, and the solution is stirred for 10 h. Reaction progress is monitored by thin-layer chromatography (dichloromethane:hexanes 1:1). The reaction mixture is extracted with distilled water and washed with dichloromethane (2×100 mL). The organic layer is isolated, dried (Na₂SO₄), filtered, and concentrated to yield the crude product, which is purified by elution through a silica gel plug (dichloromethane:hexanes 1:2). The product is a clear viscous oil (8.0 g, 40%). $^1$H NMR (400 MHZ, CDCl₃): δ 5.92 (ddt, J=17.2, 10.3, 5.7 Hz, 2H), 5.28 (dq, J=17.2, 1.6 Hz, 2H), 5.18 (dq, J=10.4, 1.4 Hz, 2H), 4.03 (dt, J=5.7, 1.4 Hz, 4H), 3.61 (s, 4H). $^{13}$C NMR (125 MHz, CDCl₃): δ 134.8, 117.1, 72.3, 69.5, 29.7, 14.1. M/z HRMS (ESI+) calculated for C₈H₁₄O₂Na [M+Na]⁺: 165.1; found: 165.1.

Comparative Example 5

Preparation of Tetrol 5

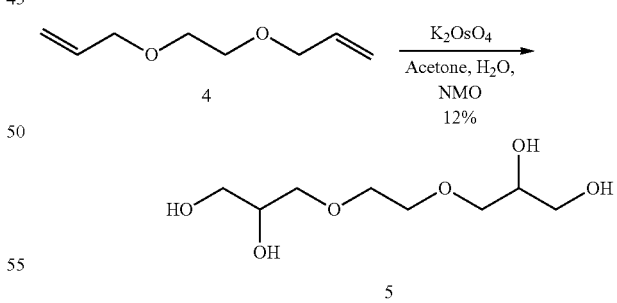

A 500-mL round-bottom flask is charged with acetone (80 mL), tert-butanol (100 mL), distilled water (100 mL), and N-methylmorpholine N-oxide (50 wt. % solution in water, 20 mL). Ethylene glycol bis(allyl ether) (8.0 g, 56 mmol) is added, and the mixture is magnetically stirred. Potassium osmate(VI) dihydrate (150 mg, 41 mmol) is added, and the mixture is allowed to react for 24 h. The reaction is quenched by adding sodium sulfite (30 g), and the mixture is stirred for 1 h. The reaction mixture is extracted with ethyl acetate (5×100 mL). The organic layer is isolated, dried (NaSO$_4$), and concentrated to give a brown oil. Flash column chromatography on 40-63 μm silica gel (methanol: dichloromethane 5:95) provides a viscous, orange oil (1.45 g, 12%). $^1$H NMR (400 MHZ, CD$_3$OD): δ 3.76 (ddd, J=11.1, 6.0, 4.7 Hz, 2H), 3.64 (s, 4H), 3.53 (m, 8H). $^{13}$C NMR (125 MHz, CDCl$_3$): δ 73.7, 72.2, 71.7, 64.4. M/z HRMS (ESI+) calculated for C$_8$H$_{18}$O$_6$Na [M+Na]$^+$: 233.23; found: 233.1.

Example 6

Small-Molecule Degradation Study

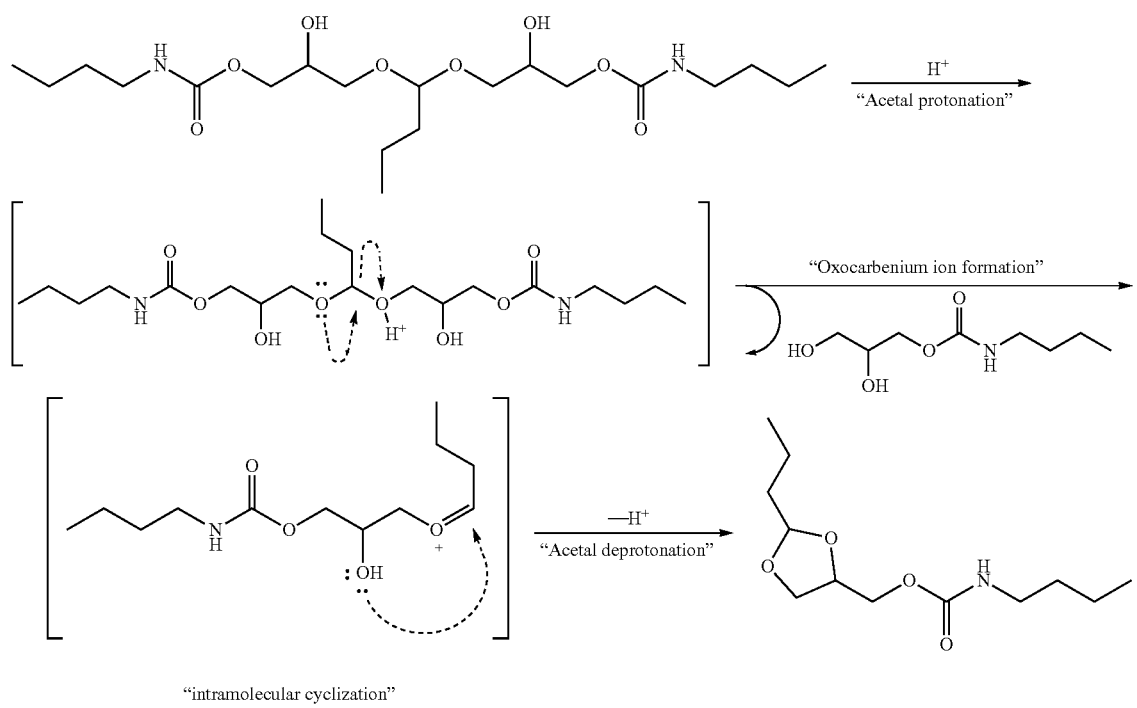

"intramolecular cyclization"

Glass vials (6-mL) are preconditioned by submerging them in 1 M acetic acid overnight, followed by rinsing with distilled water and acetone. The vials are dried in an oven for 6 h before use. Bis(carbamate) 3 (0.5 mmol) is combined in a preconditioned vial with CDCl$_3$ (or deuterated acetonitrile). In an NMR tube, a solution of the bis(carbamate) solution is combined with p-toluenesulfonic acid (3 mol %) and hexamethylbenzene (internal standard, 0.3 eq.). Degradation of the acetal is monitored in two-hour intervals.

The acetal proton of bis(carbamate) 3 appears initially as a triplet centered around 4.33 ppm. As degradation proceeds, this signal rapidly disappears over 6 h, and a new signal centered at about 4.90 ppm, a doublet of doublets, emerges (see FIG. 1). The latter signal results from formation of a new acetal proton in the 2-propyl-1,3-dioxolane ring, which is split by each proton on the nearby methylene group. The shift downfield by 0.5 ppm is consistent with formation of a five-membered ring versus the original acyclic acetal. The experiment demonstrates successful degradation using a model compound instead of a high polymer. Formation of the 1,3-dioxolane degradation product is confirmed by high-resolution mass spectrometry analysis (M/z=245.3). The expected diol coproduct (M/z=191.2) is also identified by HRMS.

Example 7 and Comparative Examples 8 and 9

Polyurethane Elastomer Syntheses

A 20-mL glass vial with a nylon cap is charged with acetal-functional tetrol 2 (104 mg, 0.5 eq.), tetrahydrofuran (0.4 mL), and a trace of a spirodibenzopyran dye. The contents are magnetically stirred under nitrogen until the tetrol dissolves. The vial is quickly opened to add a commercial prepolymer made from polypropylene glycol and TDI ("PPG-TDI," Mn=2300 g/mol, 1.9 mL, 1.0 eq.). The contents are then mixed for 1 h before the THF is removed under vacuum for 3 h. A sample of the chain-extended urethane mixture (0.3 mL) is applied to a rectangular PTFE mold and cured at 95° C. for 6 h. The resulting elastomer is stored in a desiccator for 24 h before mechanical property and degradation testing.

The same procedure is used to produce a comparative elastomer from 0.5 eq. of tetrol 5, which lacks acetal functionality (Comparative Example 8).

The same procedure is also used to produce a comparative elastomer from 0.2 eq. of tetrol 4 per equivalent of the TDI-PPG prepolymer (Comparative Example 9).

Acid Degradation Studies

Polyurethane cast films produced as described in Example 7 and Comparative Examples 8 and 9 are immersed at room temperature in vials that contain either 1 M aq. HCl or 0.1 M trichloroacetic acid in dichloromethane, and observations are made at 5 min, 1 h, 2 h, and 3 h. None of the samples significantly degrades after 3 h (or even after 3 weeks) in 1 M aq. HCl. All of the samples swell quickly in the dichloromethane solutions. The sample from Comparative Example 8, which lacks acetal functionality, swells but does not dissolve even in the presence of trichloroacetic acid. Similarly, the sample made using only 0.2 eq. of the acetal-functional tetrol (Comparative Example 9) swells but does not dissolve in the 0.1 M trichloroacetic acid/dichloromethane mixture. However, when 0.5 eq. of acetal-functional tetrol 4 is included in the polymer, the film swells within 5 minutes and degrades within 3 h. When the solvent is removed, only a thick liquid remains.

The results demonstrate that polyurethanes produced from enough of the inventive acetal-functional tetrols can degrade predictably at room temperature in the presence of dilute, acidic dichloromethane while remaining intact when exposed to only dilute aqueous acid. The additional hydroxyl functionality present in the 0.5 eq. sample may assist in depolymerization via an intramolecular cyclization reaction, whereas the 0.2 eq. sample should degrade only at the acetal link. The rapid degradation of the 0.5 eq. sample suggests that the rate of degradation is rapid only when both an acetal/ketal functionality and free hydroxyl groups are present in the polymer. The results indicate that polyurethanes made with enough of the tetrol monomer would remain functional when exposed to acid rain (pH 3.5 to 5.5) but could be converted to hydroxy-functional intermediates and repurposed under other relatively mild conditions at low energy expenditure.

Example 10

Elastomers Repurposed: Production of a Hydroxy-Functional Prepolymer

Elastomer samples prepared as in Example 7 (1.11 g) are charged to a 250-mL round-bottom flask. Trichloroacetic acid in dichloromethane (0.1 M solution, 50 mL) is added, and the mixture is stirred magnetically overnight. The reaction is quenched with saturated aq. sodium bicarbonate (15 mL), and the mixture is extracted with dichloromethane. The organic layer is washed with saturated sodium bicarbonate (2×20 mL) and brine (2×20 mL) two more times. The organic layer is dried ($Na_2SO_4$), filtered, and concentrated to obtain a viscous, yellow oil (1.01 g, 91% mass recovery). A 20-mL vial is charged with the degraded product from the elastomer (900 mg). Acetonitrile (10 mL) and 1 M HCl (0.2 mL) are added, and the mixture is stirred overnight. The reaction mixture is partitioned into ethyl acetate (5 mL) and water (5 mL). The aqueous phase is extracted with ethyl acetate (3×20 mL). The organic phases are combined, dried ($Na_2SO_4$), filtered, and concentrated under vacuum overnight to obtain the product as a light brown oil (810 mg, 93% mass recovery).

Example 11

Elastomers Repurposed: Polyurethane Adhesive from Hydroxy-Functional Prepolymer

The hydroxy-functional prepolymer from Example 10 (92 mg) is combined with dichloromethane (0.4 mL) in a 1-mL Eppendorf tube. The resulting solution is transferred to a 6-mL glass vial containing polymeric MDI ("PAPI," 18.6 mg, product of Dow). The mixture is stirred for 15 min., and dichloromethane is removed under high vacuum for 3 h. A light brown viscous liquid is obtained. A sample (10 mg) is applied to steel or glass substrates, which are overlapped and cured at 95° C. for 6 h. Samples are stored in a desiccator for 24 h before performing a lap shear test.

The steel sample holds a suspended 20-lb weight for 3 h before adhesive failure occurs with the test sample. The glass sample holds the suspended 20-lb weight for 24 h without failure.

A lap shear test is also performed on both types of samples. With the steel substrate, the adhesive based on repurposed polyurethane demonstrates shear strength comparable to that of super glue. With the inventive adhesive, the shear strength is about 0.85 MPa, versus about 1.0 MPa for super glue. For the glass substrate, super glue fails at 0.6 MPa, while the inventive sample suffers substrate failure (broken glass) before any failure of the adhesive bond.

The results demonstrate that an acetal-functional polyurethane can be degraded and repurposed as a hydroxy-functional intermediate that is useful for making a practical polyurethane adhesive with potential commercial value.

Example 12

Elastomers Repurposed: Photochromic Coating from Hydroxy-Functional Prepolymer

The hydroxy-functional prepolymer from Example 10 (90 mg), (2,4,6-trioxotriazine-1,3,5(2H,4H,6H)-trityl)-tris(hexamethylene) isocyanate (18.2 mg, product of Carbosynth Ltd.), 1',3'-dihydro-1',3',3'-trimethyl-6-nitrospiro[2H-1-benzopyran-2,2'-2 (2H)-indole], (5 wt. %), and tetrahydrofuran (0.4 mL) are combined in a 6-mL vial and stirred for 1 h. The THF is removed under high vacuum for 3 h. The monomer mixture is applied to glass slides using a paint brush, and the resulting coatings are cured at 95° C. for at least 6 h. The slides are stored at room temperature in a desiccator for at least 12 h before testing. Photochromic activity of the coating is tested by applying a Z-shaped stencil on top of the coating and irradiating it at 365 nm for 3 min. The exposed, coated section turns purple. When the same portion of the slide is subsequently exposed to white light, the Z vanishes within 0.5 h. The process is repeated four times with the same result.

Example 13

Preparation of Butyraldehyde Dicarbonate Acetal 6

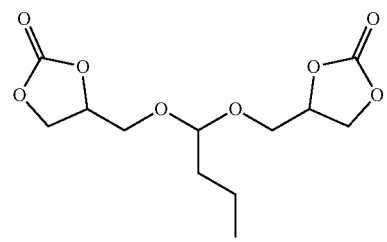

6

A solution of acetal-functional tetrol 2 (4.0 g, 17 mmol) in acetonitrile (15 mL) is combined in a round-bottom flask with dimethyl carbonate (13.0 mL, 154 mmol) and potassium carbonate granules (2.0 g). The suspension is stirred and refluxed under nitrogen using an external oil bath for 2.5 h. More dimethyl carbonate (12.0 mL, 142 mmol) is added, and the mixture is held at 50° C. for 11.5 h. The reaction mixture is cooled, diluted with dichloromethane (50 mL), vacuum filtered, and concentrated under vacuum to yield a viscous brown oil (6.0 g). The crude product is eluted through a silica plug (diameter: 4 cm; height: 6 cm) with an eluent mixture containing triethylamine (0.1 vol. %) and methanol (1 vol. %) in dichloromethane. The eluted mixture is concentrated to give a viscous yellow oil (4.4 g, 90%).

NMR analysis is consistent with the expected structures and suggests the presence of isomeric products. $^1$H NMR (CDCl$_3$): δ 4.92-4.80 (m, 2H), 4.70-4.61 (m, 1H), 4.56-4.47 (m, 2H), 4.47-4.29 (m, 2H), 3.91-3.77 (m, 2H), 3.73-3.56 (m, 2H), 1.65-1.54 (m, 2H), 1.43-1.29 (m, 2H), 0.96-0.87 (m, 3H). $^{13}$C NMR (CDCl$_3$): δ 155.1, 155.1, 130.3, 103.1, 103.0, 75.2, 75.15, 75.1, 75.0, 66.1, 66.1, 66.0, 65.3, 64.1, 63.8, 63.4, 34.8, 34.7, 34.6, 18.0, 17.9, 17.86, 13.92, 13.90. ESI-HRMS: calculated for C$_{12}$H$_{18}$O$_8$Na [M+Na]$^+$: 313.09; found 313.09.

Example 14

Preparation of a Degradable Carbamate Polymer

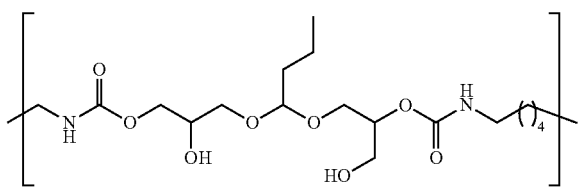

Hexamethylenediamine ("HMDA," recrystallized from cyclohexane, 0.20 g) is transferred within a glove bag under nitrogen to a tared 20-mL vial containing a magnetic stir bar. Separately, solutions of n-butyraldehyde dicarbonate acetal 6 (0.50 g) in anhydrous THF (0.5 mL) and DABCO in anhydrous THF (6 mg/mL) are prepared in the glovebag. The acetal and carbonate solutions are then transferred within the glovebag to the vial containing the HMDA by injection (mole ratio: 1:1:0.05 for diamine:dicarbonate:catalyst). Additional anhydrous THF (5×0.5 mL) is used to quantitatively transfer the dicarbonate solution via syringe to the 20-mL reaction vial, which is under nitrogen and has been removed from the glovebag. The solution is concentrated to remove most of the THF, and the concentrate is heated under nitrogen for 20 h at 80° C. using an external oil bath. The residue is dissolved in anhydrous THF (5 mL) under nitrogen and is precipitated in diethyl ether (45 mL). After isolation, the precipitation from 9:1 diethyl ether:THF is repeated two more times. Drying under high vacuum affords a sticky, yellowish white solid (0.7 g). Gel permeation chromatography: M$_n$=48 (polystyrene standards) or 10 kDa (by light scattering); polydispersity: =1.52 (polystyrene standards) or 1.66 (by light scattering). Refractive index by light scattering: d$_n$/d$_c$=0.063.

Example 15

Preparation of 1,4-Diazidobutane

A round-bottom flask is charged with 1,4-dibromobutane (38.2 g) and N,N-dimethylformamide (150 mL). A mixture of sodium azide (25.5 g) in distilled water (100 mL) is added, and the mixture is stirred magnetically for 6 h. The aqueous reaction mixture is extracted with dichloromethane. After separating the organic phase, the aqueous portion is extracted several times with more dichloromethane (500 mL total). The combined organic phases are dried (Na$_2$SO$_4$), filtered, and concentrated under reduced pressure. The diazide (24.4 g, 99%) is obtained as a clear liquid. $^1$H NMR (CDCl$_3$): δ 3.11 (ddt, 2H), 1.66 (m, 2H).

Example 16

Preparation of 4-Azido-1-aminobutane (Staudinger Reaction)

A sample of crude 1,4-diazidobutane (10.2 g), prepared as described in Example 15, is combined and stirred with 1 M aq. HCl (140 mL) and diethyl ether (50 mL). A solution of triphenylphosphine (19.1 g) in ethyl acetate (150 mL) is slowly added by addition funnel (about 12 drops per minute). The mixture is stirred overnight at room temperature, then transferred to a separatory funnel. The acidic aqueous phase is drained and retained; the organic phase (mostly ethyl acetate and triphenylphosphine oxide) is discarded. The aqueous phase is washed with ethyl acetate (200 mL) to remove any triphenylphosphine oxide, and the washed aqueous phase is then basified to pH 13 with sodium hydroxide (3.0 g). Dichloromethane (500 mL total) is used to extract the resulting mixture, which is dried (Na$_2$SO$_4$), filtered, and concentrated under reduced pressure. 4-Azido-1-aminobutane is obtained as a light-yellow liquid (2.9 g, 46%). $^1$H NMR (CDCl$_3$): δ 3.29 (t, 2H), 2.74 (t, 2H), 1.83 (s, 2H), 1.60 (m, 4H).

Example 17

Preparation of an Acetal-Functional Bis(hydroxycarbamoylazide)

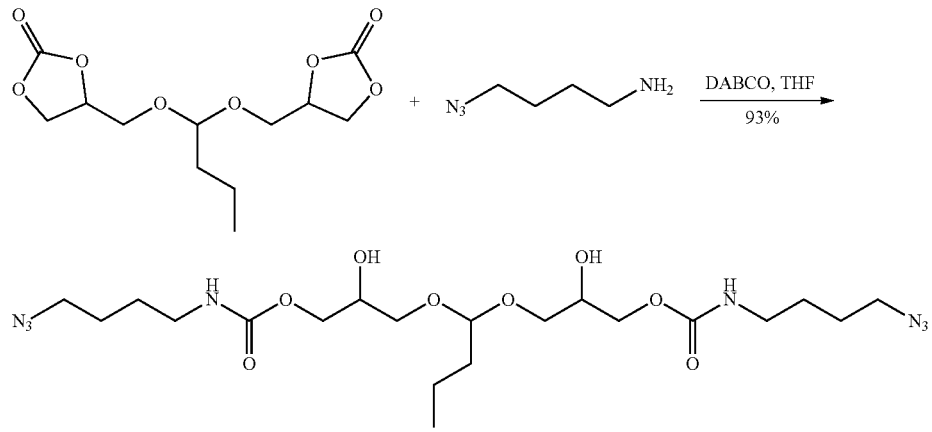

A sample of the butyraldehyde dicarbonate acetal (6) from Example 13 (4.3 g) is combined under nitrogen in a round-bottom flask with 4-azido-1-aminobutane (3.8 g), 1,4-diazabicyclo[2.2.2]octane ("DABCO," 173 mg) and tetrahydrofuran (20 mL). The mixture is stirred magnetically at 70° C. for 12 h. The mixture is concentrated under vacuum to give a viscous oil. Flash column chromatography on 40-63 µm silica gel (ethyl acetate:hexanes) and concentration of the desired fractions affords a clear, viscous oil (7.2 g, 93%). $^1$H NMR (CDCl$_3$): δ 5.19 (s, 2H), 4.86 (m, 1H), 4.59-4.54 (m, 1H), 4.24-4.09 (m, 3H), 3.99-3.95 (m, 2H), 3.80-3.50 (m, 5H), 3.31 (t, 4H), 3.23-3.28 (m, 6H), 1.67-1.58 (m, 10H), 1.40-1.32 (q, 2H), 0.95-0.90 (td, 2.85). The $^1$H NMR spectrum suggests a 7:3 ratio of secondary alcohols (shown in the structure) to primary alcohols (not shown) resulting from preferential attack of the amine at the (less-substituted) methylene carbons of the carbonate rings.

Example 18

Preparation of an Acetal-Functional Bis(hydroxycarbamoylamine)

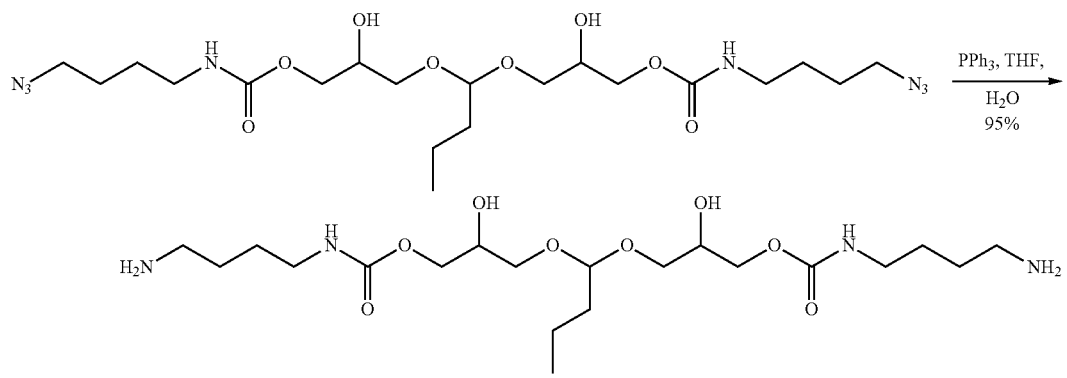

A sample of the bis(azide) from Example 17 (3.2 g) is dissolved in tetrahydrofuran (15 mL), and the solution is thoroughly cooled in an ice bath. Triphenylphosphine (6.5 g) is added, and the mixture is stirred for 1 h. The flask is removed from the ice bath, and the mixture is stirred for another 12 h at room temperature. Distilled water (1.1 mL) is added, and stirring continues for 1 h. The mixture is concentrated under vacuum. Flash column chromatography on 40-63 µm silica gel (2% aq. NH$_4$OH/methanol eluent) and concentration of the desired fractions provides 2.7 g (95%) of the desired bis(amine). $^1$H NMR (CD$_3$OD): δ 4.81 (m, 0.5H), 4.58 (d, 1H), 4.12-4.01 (m, 3H), 3.91-3.89 (p, 2H) 3.69-3.60 (m, 4H), 3.53-3.47 (m, 2H), 3.13-3.11 (m, 4H), 2.71-2.68 (m, 4H), 1.63-1.36 (m, 12H), 0.95-0.92 (m, 3H).

Example 19

Polyhydroxy Urethane (PHU) Microcapsule Synthesis by Interfacial Polymerization

Acid-degradable microcapsules are synthesized generally as described previously (see K. Broaders et al., *Chem. Commun.* 47 (2011) 665 and S. Pastine et al., *J. Am. Chem. Soc.* 131 (2009) 13586). Briefly, the bis(amine) from Example 18 (1.1 mmol) is dissolved in deionized water (1.6 mL). Separately, a solution containing a photoacid generator or "PAG" (2-(4-methoxystyryl)-4,6-bis(trichloromethyl)-1,3,5-triazine, 90 mg) and trimesoyl chloride (0.61 mmol) are dissolved in SOLVESSO™ 200 solvent (aromatic hydrocarbons, product of ExxonMobil, 2 mL). Both solutions are filtered through PTFE. A portion of the organic solution (0.5 mL) is emulsified with 0.4 M polyvinyl alcohol solution (1.5 mL) by magnetic stirring for 3 minutes at 1500 RPM. The stirring rate is reduced to 900 RPM, and the aqueous diamine solution is added dropwise by syringe. After the addition, stirring continues for 1 minute. After standing for 12 h, the resulting cured microcapsules are collected and rinsed sequentially with deionized water (100 mL), acetone (100 mL), and diethyl ether (100 mL). The weight of the microcapsules is monitored for 24 h to determine mass recovery.

Figure 2:
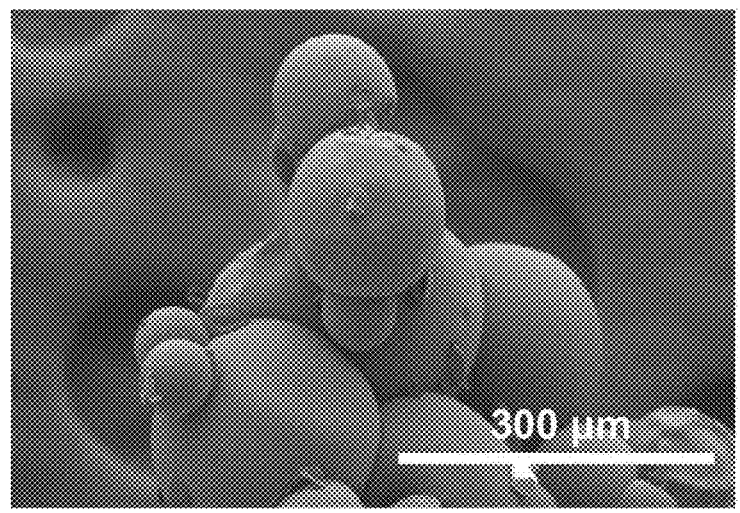
FIG. 2 is a scanning electron microscopy (SEM) image of polyhydroxy urethane (PHU) microcapsules prepared according to Example 19.

Analysis of the resulting PHU microcapsules by scanning electron microscopy (SEM) indicates that the capsules generally have smooth outer shells, a shell thickness of 3-4 µm, and diameters mostly in the 40-150 µm range (see FIG. 2).

Comparative Example 20

Acid-Triggered Degradation of Microcapsules (No Added PAG)

Figure 3:
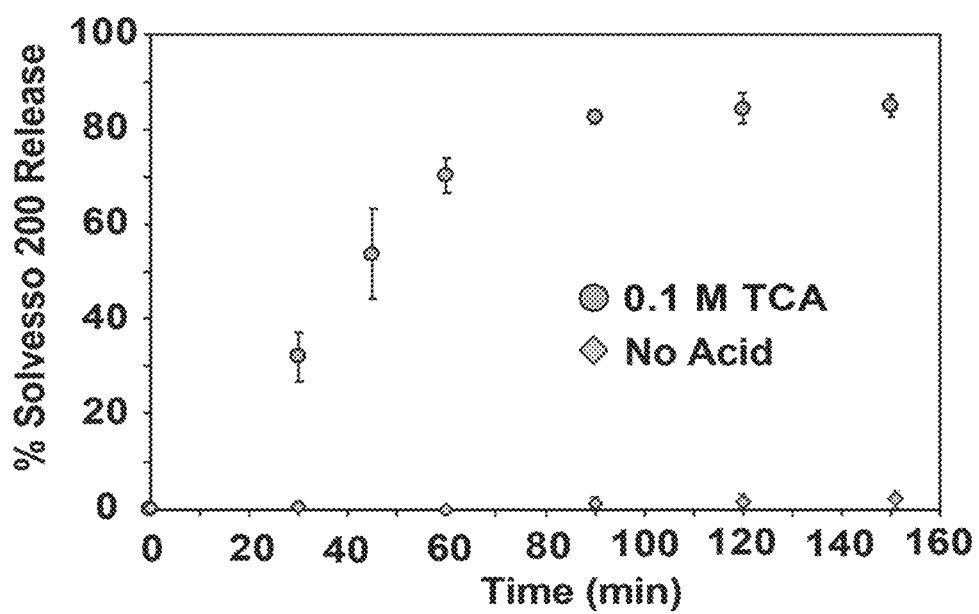
FIG. 3 is a kinetic profile showing how PHU microcapsules degrade and release core material (SOLVESSO™ 200 aromatic solvent) when placed in decane/toluene solvent with or without 0.1 M trichloroacetic acid.

The procedure of Example 19 is generally followed to produce degradable microcapsules, except that the PAG component is omitted. Microcapsules are combined with a solution of decane/toluene or a solution of decane/toluene that contains 0.1 M trichloroacetic acid (TCA). Gas chromatography is used to measure the degree of release of SOLVESSO™ solvent from the microcapsules as a function of time. Results appear in FIG. 3. As shown in the figure, when the solvent contains no acid, the microcapsules remain intact, and little SOLVESSO™ solvent is detected within the 2.5-hour test. In contrast, when TCA is present in the decane/toluene solvent, the TCA triggers degradation of the microcapsules and 90% of the SOLVESSO™ solvent is released within 1.5 h.

The results demonstrate that acid can be used to trigger degradation of PHU microcapsules under nonaqueous conditions.

Comparative Example 21

Non-Degradable Microcapsule Preparation and Testing

The procedure of Example 19 is generally followed using diethylenetriamine (DETA) instead of the bis(amine) from Example 18 to generate non-degradable microcapsules. In one experiment ("21A"), the microcapsules include both the PAG component and 4-(dimethylamino) azobenzene (methyl yellow), a pH indicator. In another experiment ("21B"), microcapsules are formulated from DETA and include methyl yellow but no PAG component.

Samples (150 mg) of the microcapsules prepared in experiments 21A and 21B are placed in a 20-mL glass vial and irradiated with 365-nm LED UV light for 10 minutes. Prior to irradiation, SEM analysis shows that the microcapsules from both experiments 21A and 21B are intact and yellow, indicating an internal pH>4. Upon irradiation, SEM inspection indicates no change in the microcapsules in either color or structure from experiment 21B, which lacks the PAG. This demonstrates no significant generation of acid within the hydrocarbon-filled capsules. In contrast, the microcapsules from experiment 21A are intact but turn red within 10 minutes of irradiation, indicating that conditions within the capsules have become much more acidic (pH<2), although the capsule walls remain robust. Irradiation of PAG generates chlorine radicals by homolytic cleavage that can abstract a hydrogen atom to generate HCl. The results demonstrate that the PAG can respond to UV light within an intact microcapsule.

Example 22

Testing of a Degradable Polyhydroxy Urethane (PHU) Microcapsule

PHU microcapsules containing PAG prepared as described in Example 19 are irradiated as described in Comparative Example 21 with 365-nm LED UV light for 40 min, and observations are made at 1 min, 10 min, 20 min, and 40 min (experiment "22A"). Within 1 minute of exposure to UV radiation, capsule collapse is evident; within 10-20 minutes, the hydrocarbon solvent is released from the capsules. In a comparative experiment ("22B"), PHU microcapsules prepared in the absence of the PAG are irradiated in the same way, but no degradation occurs.

Comparative Example 23

Unstable Microcapsules from a Long-Chain Diamine Lacking Neighboring Hydroxyl Groups Microcapsules containing PAG are prepared as described in Example 19 except that the diamine shown below, an analog of the hydroxy-functional diamine used in Example 19, is used:

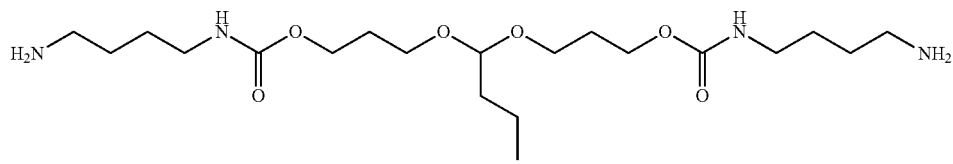 [SMILES: CCCC(OCCCOC(=O)NCCCCN)OCCCOC(=O)NCCCCN]

Figure 4:
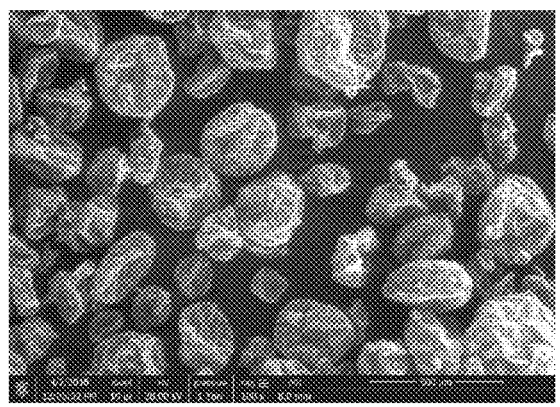
FIG. 4 is an SEM image of unstable microcapsules prepared as described in Comparative Example 23.

SEM analysis of the resulting capsules reveals collapsed capsules (FIG. 4), possibly due to the lack of hydroxyl functionality.

Example 24

Demonstrating the Value of a Neighboring Hydroxyl Group

Stable microcapsules having acetal functionality but no hydroxyl groups are generated by reducing the chain length of the diamine. In this case, the diamine is synthesized in two steps from n-butyraldehyde and commercially available N-(3-hydroxypropyl) phthalimide using known chemistry. Acetalization of the protected 3-hydroxypropylamine is followed by basic hydrolysis of the resulting bis(phthalimide) to give the acetal-functional diamine:

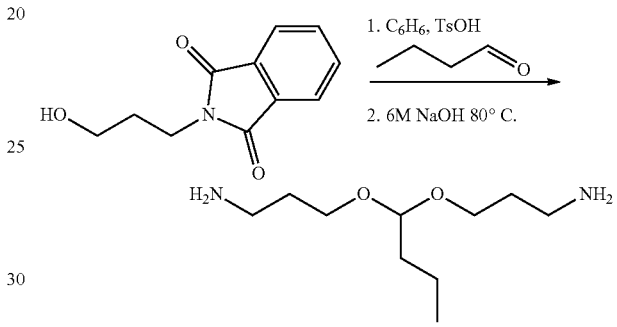

Degradable microcapsules containing PAG are then prepared as previously described and compared with the degradable PHU microcapsules prepared as in Example 19.

Figure 5:
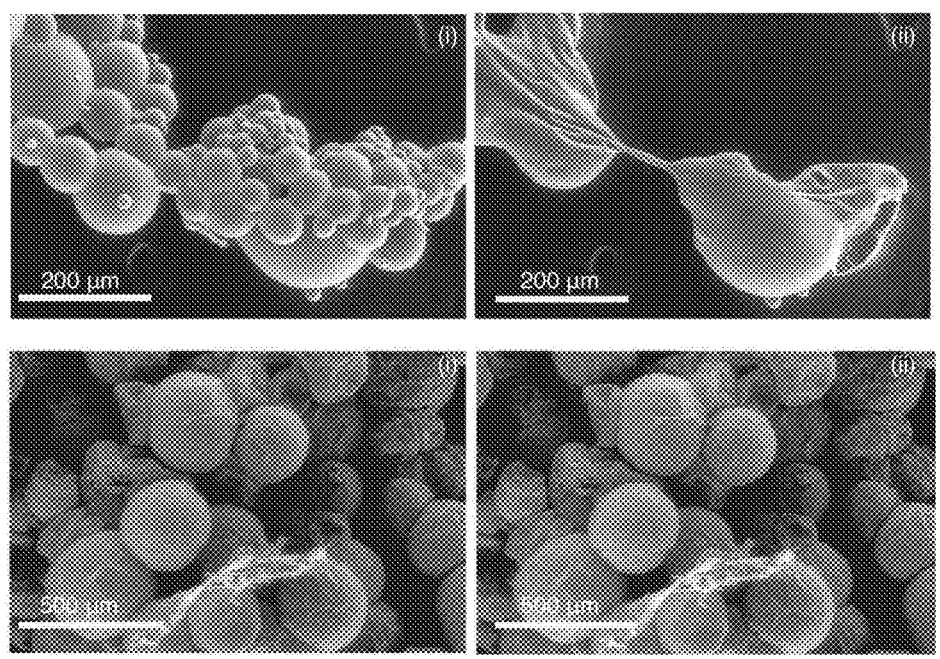
FIG. 5. shows SEM images of PAG-loaded PHU microcapsules before and after irradiation with UV at 365 nm for 8 minutes (top pair of photos) and SEM images of PAG-loaded control microcapsules before and after irradiation with UV at 365 nm for 20 minutes (bottom pair of photos).

In theory, both sets of microcapsules should be prone to disintegration upon irradiation and generation of HCl within the microcapsule. SEM scans show that irradiation for 20 minutes with UV light at 365 nm of PAG-loaded microcapsules based on the acetal-functional diamine that lacks hydroxyl functionality has little or no effect on microcapsule morphology (FIG. 5, lower pair of micrographs). In contrast, when neighboring hydroxyl groups are present, disintegration and coalescence of the microcapsules is evident from the SEM image within 8 minutes of irradiation (FIG. 5, upper pair of micrographs). The results demonstrate that a neighboring hydroxyl group may be needed to promote shell degradation of microcapsules in this hydrophobic environment. The results are consistent with the "CATCH cleavage" mechanism (described earlier) in which formation of a stable cyclic acetal with the available neighboring hydroxyl group can help to drive the degradation process.

LC-MS Analysis

Figure 6:
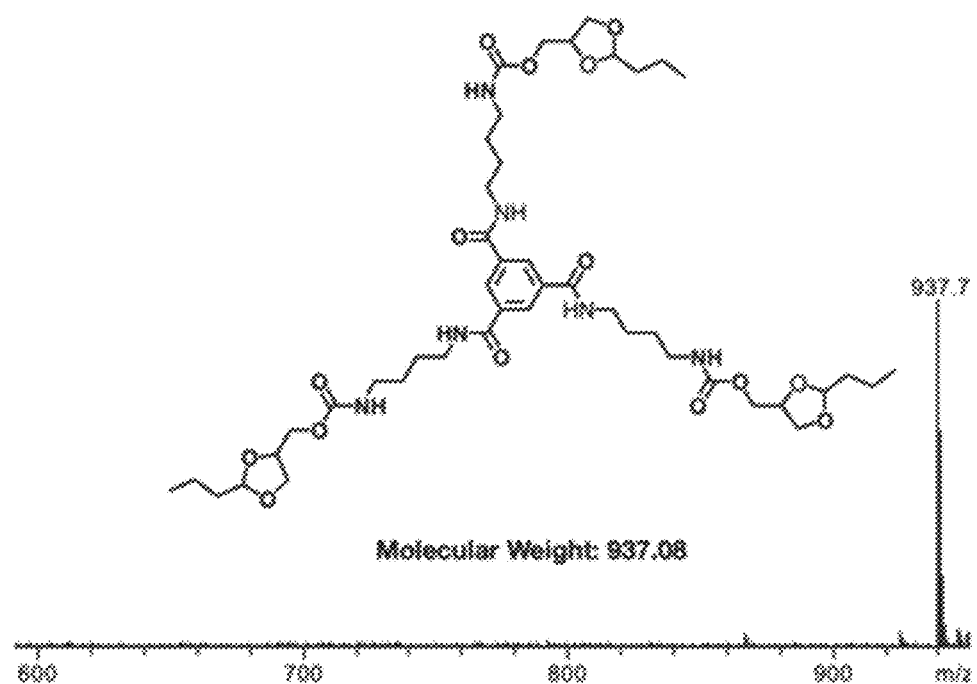
FIG. 6 shows the structure and mass spectrum of a tris(cyclic acetal) isolated by liquid chromatography as a microcapsule degradation product.

Analysis of degraded microcapsules using liquid chromatography/mass spectrometry (LC-MS) analysis using a Waters SYNAPT™ G2 Si electrospray ionization (ESI)

mass spectrometer reveals LC peaks that correspond to CATCH cleavage reaction products. Specifically, mass spectrometry analysis reveals one major product to be the tris(cyclic acetal), with far lesser amounts of the corresponding bis- and monocyclic acetals identified. FIG. 6 shows the structure of the tris(cyclic acetal) isolated by LC along with its mass spectrum.

The preceding examples are mere illustrations; the following claims define the inventive subject matter.

We claim:

1. A hydroxyacetal or hydroxyketal monomer of the formula:

wherein C is an acetal or ketal carbon; each of $R^1$ and $R^2$ is hydrogen or a $C_1$-$C_{10}$ alkyl group or a $C_6$-$C_{10}$ aryl, aralkyl, or alkaryl group; and X and Z are the same or different $C_3$-$C_{20}$ hydroxyalkyl or polyhydroxyalkyl groups such that: (a) each of X and Z has at least one hydroxyl group; (b) one of X or Z has two or more hydroxyl groups; and (c) one or both of the hydroxyalkyl or polyhydroxyalkyl groups has a free or protected hydroxyl group located on a carbon that is γ- or δ- to the acetal or ketal carbon, and
wherein one of X or Z is a residue from propylene glycol, diethylene glycol, dipropylene glycol, triethylene glycol, tripropylene glycol, 2-methyl-1,3-propanediol, neopentyl glycol, or 1,6-hexanediol.

2. The monomer of claim 1 wherein the protected hydroxyl group incorporates a photocleavable protecting group.

3. An acid-degradable polyurethane or melamine product comprising one or more recurring units of the monomer of claim 1.

4. A mixture comprising a hydroxy-functional intermediate, said mixture made by acid-catalyzed degradation of the polyurethane or melamine product of claim 3.

5. A polyurethane coating, adhesive, sealant, elastomer, or foam made from the mixture of claim 4.

6. The adhesive of claim 5 further made from polymeric MDI.

7. A photochromic coating comprising the mixture of claim 4 and a spiropyran dye.

8. A melamine product made by reacting the mixture of claim 4 with hexakis(methoxymethyl)melamine.

9. A radiation-curable resin made by reacting the mixture of claim 4 with a (meth)acrylic acid or (meth)acrylate ester.

10. UV light-degradable microcapsules comprising:
(a) a core comprising an oil-based active material and a photoacid generator; and
(b) a degradable shell surrounding the core; the shell comprising a crosslinked polyester, wherein the polyester is made by reacting the monomer of claim 1 with a di- or polycarboxylic acid, ester, or halide in an aqueous emulsion under conditions effective to produce the light-degradable microcapsules.

11. The microcapsules of claim 10 wherein the oil-based active material is a flavor, a fragrance, an indicator for a coating, a sunscreen, a biocide, an agricultural active, a fire retardant, or another beneficial agent.

12. A process which comprises exposing the microcapsules of claim 10 to UV light to induce inside-out, acidic degradation of the microcapsules and liberate the oil-based active material.

13. The monomer of claim 1 wherein the one of X or Z is the residue from propylene glycol, diethylene glycol or dipropylene glycol.

14. The monomer of claim 1 wherein the one of X or Z is the residue from triethylene glycol, tripropylene glycol, 2-methyl-1,3-propanediol, or neopentyl glycol.

15. The monomer of claim 1 wherein the one of X or Z is the residue from 1,4-butanediol, or 1,6-hexanediol.

* * * * *